(12) United States Patent
Speronello et al.

(10) Patent No.: US 8,524,202 B2
(45) Date of Patent: *Sep. 3, 2013

(54) TOOTH WHITENING COMPOSITIONS AND METHODS

(75) Inventors: Barry Keven Speronello, Montgomery Township, NJ (US); Frank S. Castellana, Princeton, NJ (US); Linda Hratko, Colonia, NJ (US)

(73) Assignee: BASF Corporation, Florham Park, NJ (US)

( * ) Notice: Subject to any disclaimer, the term of this patent is extended or adjusted under 35 U.S.C. 154(b) by 316 days.

This patent is subject to a terminal disclaimer.

(21) Appl. No.: 12/502,761

(22) Filed: Jul. 14, 2009

(65) Prior Publication Data
US 2010/0015067 A1 Jan. 21, 2010

Related U.S. Application Data

(60) Provisional application No. 61/135,011, filed on Jul. 15, 2008, provisional application No. 61/106,026, filed on Oct. 16, 2008, provisional application No. 61/150,685, filed on Feb. 6, 2009.

(51) Int. Cl.
*A61K 8/20* (2006.01)

(52) U.S. Cl.
USPC .................. 424/53; 424/48; 424/49; 433/215

(58) Field of Classification Search
USPC ...................................... 424/49, 53
See application file for complete search history.

(56) References Cited

U.S. PATENT DOCUMENTS

| | | |
|---|---|---|
| 2,071,091 A | 2/1937 | Taylor |
| 2,701,781 A | 2/1955 | de Guevara |
| 3,123,521 A | 3/1964 | Wentworth et al. |
| 4,060,600 A | 11/1977 | Vit |
| 4,104,190 A | 8/1978 | Hartshorn |
| 4,177,199 A | 12/1979 | Granatek et al. |
| 4,330,531 A | 5/1982 | Alliger |
| 4,585,482 A | 4/1986 | Tice |
| 4,683,039 A | 7/1987 | Twardowski |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ractliff |
| 4,851,213 A | 7/1989 | Ratcliff |
| 4,855,135 A | 8/1989 | Ratcliff |
| 4,886,657 A | 12/1989 | Ratcliff |
| 4,889,714 A | 12/1989 | Ratcliff |
| 4,925,656 A | 5/1990 | Ratcliff |
| 4,975,285 A | 12/1990 | Ratcliff |
| 5,200,171 A | 4/1993 | Ratcliff |
| 5,227,168 A | 7/1993 | Chvapil |
| 5,281,412 A | 1/1994 | Lukacovic |
| 5,348,734 A | 9/1994 | Ratcliff |
| 5,384,134 A | 1/1995 | Kross et al. |
| 5,399,288 A | 3/1995 | Marzouk |
| 5,407,656 A | 4/1995 | Roozdar |
| 5,489,435 A | 2/1996 | Ratcliff |
| 5,597,561 A | 1/1997 | Kross |
| 5,618,550 A | 4/1997 | Ratcliff |
| 5,651,996 A | 7/1997 | Roozdar |
| 5,719,100 A | 2/1998 | Zahradnik |
| 5,820,822 A | 10/1998 | Kross |
| 5,879,691 A | 3/1999 | Sagel |
| 5,944,528 A | 8/1999 | Montgomery |
| 6,007,735 A | 12/1999 | Creed |
| 6,039,934 A | 3/2000 | Alliger |
| 6,046,243 A | 4/2000 | Wellinghoff |
| 6,077,495 A | 6/2000 | Speronello |
| 6,077,502 A | 6/2000 | Witt |
| 6,106,284 A | 8/2000 | Cronin |
| 6,238,643 B1 | 5/2001 | Thangaraj |
| 6,280,775 B1 | 8/2001 | Sasson et al. |
| 6,287,551 B1 | 9/2001 | Ratcliff |
| 6,294,108 B1 | 9/2001 | Speronello |
| 6,294,510 B1 | 9/2001 | Norman |
| 6,312,670 B1 | 11/2001 | Montgomery |
| 6,365,131 B1 | 4/2002 | Doshi et al. |
| 6,379,658 B1 | 4/2002 | Marano |
| 6,425,759 B1 | 7/2002 | Cronin |
| 6,432,322 B1 | 8/2002 | Speronello |
| 6,432,387 B1 | 8/2002 | Kaizuka |
| 6,479,037 B1 | 11/2002 | Montgomery |
| 6,500,408 B2 | 12/2002 | Chen |
| 6,551,579 B2 | 4/2003 | Sagel |

(Continued)

FOREIGN PATENT DOCUMENTS

| | | |
|---|---|---|
| DE | 198 54 349 A1 | 5/2000 |
| DE | 19854349 A1 | 5/2000 |

(Continued)

OTHER PUBLICATIONS

Office action mailed Aug. 10, 2011; U.S. Appl. No. 12/502781, filed Jul. 14, 2009.
US EPA Correspondence dated Jun. 17, 2010 regarding PUROGENE product label [online] [retrieved Aug. 25, 2011] Retrieved from the Internet: <URL: http://www.epa.gov/pesticides/chem_search/ppls/009804-00005-20100617.pdf>.
US EPA Correspondence dated Jun. 18, 1985 regarding Odorid product label [online] [retrieved Aug. 25, 2011] Retrieved from the Internet: <URL: http://www.epa.gov/pesticides/chem_search/ppls/009804-00003-19850618.pdf>.
Office Action issued Dec. 28, 2010 in U.S. Appl. No. 12/502,781, filed Jul. 14, 2009.
"Carnebon® 200 Stabilized Chlorine Dioxide Solution" Material Safety Data Sheet, DuPont, Wilmington DE, Apr. 5, 2011. [online], [retrieved Jul. 22, 2011] Retrieved from DuPont website using Internet <URL: http://msds.dupont.com/msds/pdfs/EN/PEN_09004a35804e6763.pdf>.
Office Action dated Dec. 29, 2010 in U.S. Appl. No. 12/502,356.
Office Action dated Aug. 10, 2011 in U.S. Appl. No. 12/502,356.
Office Action dated Sep. 12, 2011 in U.S. Appl. No. 12/502,326.

(Continued)

*Primary Examiner* — Walter Webb
(74) *Attorney, Agent, or Firm* — Elizabeth Pietrowski

(57) ABSTRACT

Non-cytotoxic compositions for tooth whitening are disclosed. Methods of their use are also provided.

7 Claims, 4 Drawing Sheets

(56) References Cited

U.S. PATENT DOCUMENTS

| | | |
|---|---|---|
| 6,582,682 B2 | 6/2003 | Stier |
| 6,669,931 B2 | 12/2003 | Lynch |
| 6,682,721 B2 | 1/2004 | Kim |
| 6,699,404 B2 | 3/2004 | Speronello |
| 6,759,030 B2 | 7/2004 | Kosti |
| 6,848,905 B2 | 2/2005 | Jacobs |
| 6,896,518 B2 | 5/2005 | Jacobs |
| 6,964,571 B2 | 11/2005 | Andersen |
| 7,004,756 B2 | 2/2006 | Andersen |
| 7,040,897 B2 | 5/2006 | Fischer |
| 7,087,190 B2 | 8/2006 | Hei |
| 7,087,208 B2 | 8/2006 | Sampson |
| 7,182,883 B2 | 2/2007 | Speronello |
| 7,220,367 B2 | 5/2007 | Speronello |
| 7,229,647 B2 | 6/2007 | Lee |
| 7,273,567 B1 | 9/2007 | Wellinghoff |
| 7,514,019 B2 | 4/2009 | Martin |
| 7,534,368 B2 | 5/2009 | Martin |
| 7,875,460 B2 | 1/2011 | Ratcliff |
| 8,303,939 B2 | 11/2012 | Speronello et al. |
| 8,377,423 B2 | 2/2013 | Speronello et al. |
| 2002/0137728 A1 | 9/2002 | Montgomery |
| 2003/0152528 A1 | 8/2003 | Singh |
| 2003/0228264 A1 | 12/2003 | Perna |
| 2003/0235549 A1 | 12/2003 | Singh |
| 2006/0024369 A1 | 2/2006 | Speronello |
| 2006/0045855 A1 | 3/2006 | Sasson |
| 2006/0088498 A1 | 4/2006 | Martin |
| 2006/0099550 A1 | 5/2006 | Faasse |
| 2006/0169949 A1 | 8/2006 | Speronello |
| 2006/0183080 A1 | 8/2006 | Nosov |
| 2006/0223033 A1 | 10/2006 | McLean |
| 2006/0292090 A1 | 12/2006 | Sharma |
| 2007/0172412 A1 | 7/2007 | Hratko |
| 2007/0202095 A1 | 8/2007 | Speronello |
| 2007/0231277 A1 | 10/2007 | Sharma |
| 2007/0298380 A1 | 12/2007 | Allred |
| 2008/0023668 A1 | 1/2008 | Callerame |
| 2008/0025925 A1 | 1/2008 | Allred |
| 2008/0041400 A1 | 2/2008 | Darnell |
| 2009/0016973 A1 | 1/2009 | Ratcliff |
| 2009/0017548 A1 | 1/2009 | Ratcliff |
| 2010/0009009 A1 | 1/2010 | Young |
| 2010/0012891 A1 | 1/2010 | Speronello et al. |
| 2010/0012892 A1 | 1/2010 | Speronello et al. |
| 2010/0015066 A1 | 1/2010 | Speronello et al. |
| 2010/0015251 A1 | 1/2010 | Speronello et al. |
| 2010/0062076 A1 | 3/2010 | Speronello et al. |
| 2010/0074970 A1 | 3/2010 | Ratcliff |
| 2010/0221198 A1 | 9/2010 | Ratcliff |
| 2010/0233101 A1 | 9/2010 | Grootveld |
| 2011/0229422 A1 | 9/2011 | Speronello et al. |
| 2011/0236323 A1 | 9/2011 | Speronello et al. |
| 2011/0318282 A1 | 12/2011 | Ratcliff |

FOREIGN PATENT DOCUMENTS

| | | |
|---|---|---|
| EP | 0 371 728 A1 | 6/1990 |
| JP | 60105610 | 6/1985 |
| WO | WO-90/06126 A1 | 6/1990 |
| WO | 98004235 A1 | 2/1998 |
| WO | WO-2004/028498 A1 | 4/2004 |
| WO | WO-2004/062660 A1 | 7/2004 |
| WO | WO-2005/011582 A2 | 2/2005 |
| WO | WO 2007/062347 A2 | 5/2007 |
| WO | WO 2007/079287 A2 | 7/2007 |
| WO | 20070131970 A1 | 11/2007 |
| WO | WO 2007/131970 A1 | 11/2007 |

OTHER PUBLICATIONS

Office Action dated Mar. 2, 2011 in U.S. Appl. No. 12/502,326.
Office Action dated Apr. 27, 2011 in U.S. Appl. No. 12/502,639.
International Search Report published Mar. 11, 2010 in PCT International Application No. PCT/US2009/050541.
International Preliminary Report on Patentability issued Jan. 18, 2011 in PCT International Application No. PCT/US2009/050541.
Communication dated Jul. 26, 2011 in European Patent Application No. 09 790 352.0.
International Search Report published Mar. 11, 2010 in PCT International Application No. PCT/US2009/050638.
International Preliminary Report on Patentability issued Jan. 18, 2011 in PCT International Application No. PCT/US2009/050638.
Office Action dated Dec. 20, 2011 in U.S. Appl. No. 12/502,925.
Office Action dated Jun. 10, 2011 in U.S. Appl. No. 12/502,925.
International Search Report published Mar. 11, 2010 in PCT International Application No. PCT/US2009/050629.
Office Action dated Mar. 7, 2011 in U.S. Appl. No. 12/502,664.
Office Action dated Dec. 14, 2011 in U.S. Appl. No. 12/502,895.
Office Action dated Feb. 15, 2012 in U.S. Appl. No. 12/502,907.
Office Action dated Feb. 2, 2012 in U.S. Appl. No. 13/054,493.
Office Action dated Nov. 10, 2011 in U.S. Appl. No. 13/054,494.
Office Action dated Jun. 29, 2011 in U.S. Appl. No. 12/502,895.
Office Action dated Jul. 5, 2011 in U.S. Appl. No. 12/502,907.
Mokhlis et al., "A clinical evaluation of carbamide peroxide and hydrogen peroxide whitening agents during daytime use," *J. Am. Dent. Assoc.* 131: 1269-77 2000.

TOOTH WHITENING COMPOSITIONS AND METHODS

CROSS-REFERENCE TO RELATED APPLICATIONS

This application claims the benefit pursuant to 35 U.S.C. §119(e) of U.S. Provisional Application Nos. 61/135,011, filed on Jul. 15, 2008; 61/106,026, filed Oct. 16, 2008; and 61/150,685, filed Feb. 6, 2009, each of which is hereby incorporated by reference in its entirety herein.

BACKGROUND

Efforts to whiten teeth have a long history, thought to date back to the Ancient Egyptians. Modern science has provided a detailed understanding of the factors that contribute to tooth color, which has enabled improved products and methods for whitening. The normal shade of teeth is determined by the natural off-white tints of the enamel and the dentin beneath. Extrinsic and intrinsic staining also contribute to tooth color.

Extrinsic staining refers to surface stains, such as those caused by tea, coffee, red wine, and other foods rich in polyphones. Extrinsic staining primarily occurs as a result of charged surface interactions between the positively-charged food molecules and the negatively-charged tooth pellicle, the protein film on the tooth surface that is derived from salivary proteins. Extrinsic stains are removed through the use of surfactants and/or abrasives, which cause their physical removal from the tooth surface.

Intrinsic staining refers to stains that exist below enamel surface, or that penetrate below enamel surface. Intrinsic staining can happen when food molecules seep into enamel flaws and cracks, or, in some cases, between enamel rods. Intrinsic discoloration can also occur following a change to the structural composition or thickness of the dental hard tissues. Certain metabolic diseases and tooth trauma can also cause intrinsic staining. Tetracyline also causes intrinsic staining.

Removal of intrinsic staining is more difficult and time consuming than removal of extrinsic staining. Intrinsic stain removal can be achieved by a variety of methods including use of peroxides or peroxide analogs, with or without chemical, light or heat activation, to bleach the stains. This method oxidizes organic compounds within the enamel and dentin, thereby changing colored materials to non-colored materials; it does not remove the stain itself. Acids and dehydration methods, which lead to opacification of enamel to obscure the subsurface stains, are also used to remove or mask intrinsic staining.

Tooth whitening products are available over-the-counter and as professional services in a dentist's office. Over-the-counter products typically contain carbamide peroxide or hydrogen peroxide as the bleaching agent. These products have concentrations of up to 21% carbamide peroxide (equivalent to 7% hydrogen peroxide) or as much as 10% hydrogen peroxide. They also contain carbomers (for thickening and control) and acidifiers (for peroxide stabilization in aqueous solution), or alternatively have an anhydrous glycerin base. In-office treatments generally use hydrogen peroxide as the oxidizer, at concentrations of 15% or more, and typically in the 25 to 35% range. At these high concentrations, rubber dams, or liquid dams with proper suction, must be used to prevent gingival irritation and ingestion. Additionally, due to their high strengths, products for professional treatment require more thickener and more acidification to make them stable, compared to home-use products. Furthermore, professional chair-side formulas have a secondary and often even tertiary and quaternary activators to stimulate a more rapid result. These activators take the form of pH modifiers, light sources, and heat sources.

Tooth whitening products, both over-the counter and particularly professional treatments, have several unpleasant side effects, including tooth sensitivity, soft tissue irritation and tooth surface changes.

Transient tooth sensitivity is the most common side effect reported. Hydrogen peroxide and carbamide peroxide have not been found to induce pathological pulpal changes in testing, although 10% carbamide peroxide has been reported as causing mild, reversible histological changes. It is believed that the hypersensitivity associated with whitening is caused by dehydration, due to the acidified and thickened, substantially anhydrous, hydrophillic gels used in the peroxide formulations and that are held against the teeth. Dehydration results in a negative osmotic pressure and in odontoblastic processes being drawn into the dentinal tubules. Other factors that may contribute to dehydration include whitening lights used in in-office treatments. While sensitivity may be transient, it is a very undesirable side effect.

Oral mucosa irritation is the second most-common side effect reported. Systems using higher concentrations of hydrogen peroxide or carbamide peroxide result in more gingival irritation than lower concentration formulations. While peroxide is regarded as safe at low concentrations, peroxide has the potential to induce cell changes at high concentrations over an extended period of time.

Tooth surface changes have been observed for hydrogen peroxide and carbamide peroxide in in-vitro testing. Although recent reports on this issue have conflicting results, this aspect of tooth whitening products currently available remains a point of concern. In addition, tooth whitening formulations are usually acidic; acids can decalcify and etch teeth, causing a temporary opacification of underlying discolorations. These side effects often result in the need for remineralization therapies in connection with tooth whitening treatment, particularly those using professional products.

Another problem with current tooth whitening formulations is rebound. Rebound is the phenomenon wherein stains re-appear after a relatively short period of time after tooth whitening. The time that elapses post-treatment before this occurs varies from a few days to weeks, while other studies claim up to 47 months before any rebound effect occurs (Leonard et al., 2001, *J. Esthet. Restor. Dent.* 13(6): 357-369). One study found a rebound in 40% of patients at six months with use of concentrations ranging from 16%-18% carbamide peroxide (Brunton et al., 2004, *Oper. Dent.* 29(6): 623-626).

Chlorine dioxide ($ClO_2$) has been suggested as an alternative to peroxide based bleaching agents for tooth whitening applications. Chlorine dioxide ($ClO_2$) is well known as a disinfectant as well as a strong oxidizing agent. The bactericidal, algaecidal, fungicidal, bleaching, and deodorizing properties of chlorine dioxide are also well known.

Chlorine dioxide ($ClO_2$) is a neutral compound of chlorine in the +IV oxidation state. It disinfects by oxidation; however, it does not chlorinate. It is a relatively small, volatile, and highly energetic molecule, and a free radical even in dilute aqueous solutions. Chlorine dioxide functions as a highly selective oxidant due to its one-electron transfer mechanism in which it is reduced to chlorite ($ClO_2^-$). The pKa for the chlorite ion/chlorous acid equilibrium, is extremely low at pH 1.8. This is remarkably different from the hypochlorous acid/hypochlorite base ion pair equilibrium found near neutrality, and indicates that the chlorite ion will exist as the dominant species in drinking water.

One of the most important physical properties of chlorine dioxide is its high solubility in water, particularly in chilled water. In contrast to the hydrolysis of chlorine gas in water, chlorine dioxide in water does not hydrolyze to any appreciable extent, but remains in solution as a dissolved gas.

The traditional method for preparing chlorine dioxide involves reacting sodium chlorite with gaseous chlorine ($Cl_2$ (g)), hypochlorous acid (HOCl), or hydrochloric acid (HCl). The reactions are:

$$2NaClO_2 + Cl_2(g) = 2ClO_2(g) + 2NaCl \quad [1a]$$

$$2NaClO_2 + HOCl = 2ClO_2(g) + NaCl + NaOH \quad [1b]$$

$$5NaClO_2 + 4HCl = 4ClO_2(g) + 5NaCl + 2H_2O \quad [1c]$$

Reactions [1a] and [1b] proceed at much greater rates in acidic medium, so substantially all traditional chlorine dioxide generation chemistry results in an acidic product solution having a pH below 3.5. Also, because the kinetics of chlorine dioxide formation are high order in chlorite anion concentration, chlorine dioxide generation is generally done at high concentration (>1000 ppm), which must be diluted to the use concentration for application.

Chlorine dioxide may also be prepared from chlorate anion by either acidification or a combination of acidification and reduction. Examples of such reactions include:

$$2NaClO_3 + 4HCl \rightarrow 2ClO_2 + Cl_2 + 2H_2O + 2NaCl \quad [2a]$$

$$2HClO_3 + H_2C_2O_4 \rightarrow 2ClO_2 + 2CO_2 + 2H_2O \quad [2b]$$

$$2NaClO_3 + H_2SO_4 + SO_2 \rightarrow 2ClO_2 + 2NaHSO_4 \quad [2c]$$

At ambient conditions, all reactions require strongly acidic conditions; most commonly in the range of 7-9 N. Heating of the reagents to higher temperature and continuous removal of chlorine dioxide from the product solution can reduce the acidity needed to less than 1 N.

A method of preparing chlorine dioxide in situ uses a solution referred to as "stabilized chlorine dioxide." Stabilized chlorine dioxide solutions contain little or no chlorine dioxide, but rather, consist substantially of sodium chlorite at neutral or slightly alkaline pH. Addition of an acid to the sodium chlorite solution activates the sodium chlorite, and chlorine dioxide is generated in situ in the solution. The resulting solution is acidic. Typically, the extent of sodium chlorite conversion to chlorine dioxide is low and a substantial quantity of sodium chlorite remains in the solution.

U.S. Pat. No. 6,582,682 discloses an oral care composition comprising "stabilized chlorine dioxide" that, upon exposure to the mildly acidic pH in the oral cavity, produces chlorine dioxide.

U.S. Pat. No. 6,479,037 discloses preparing a chlorine dioxide composition for tooth whitening wherein the composition is prepared by combining a chlorine dioxide precursor (CDP) portion with an acidulant (ACD) portion. The CDP portion is a solution of metal chlorite at a pH greater than 7. The ACD is acidic, preferably having a pH of 3.0 to 4.5. The CDP is applied to the tooth surface. The ACD is then applied over the CDP to activate the metal chlorite and produce chlorine dioxide. The pH at the contact interface is preferably less than 6 and, most preferably, in the range of about 3.0 to 4.5. Thus, the resulting chlorine dioxide composition on the tooth surface is acidic. Additionally, this method exposes the oral mucosa to possible contact with a strongly highly acidic reagent (ACD).

There is a need in the art for tooth whitening compositions and methods with reduced side effects.

SUMMARY

The following embodiments meet and address these needs. The following summary is not an extensive overview. It is intended to neither identify key or critical elements of the various embodiments, not delineate the scope of them.

In one aspect, a method of whitening a tooth surface is provided. The method comprises contacting a surface of a tooth with an efficacious amount of a substantially non-cytotoxic composition, wherein the composition comprises a bleaching agent that whitens the contacted tooth surface, and wherein the bleaching agent is chlorine dioxide. In an embodiment, the composition is also substantially non-irritating. In some embodiments, the substantially non-cytotoxic composition comprises less than about 0.2 milligrams oxychlorine anion per gram composition.

In an embodiment, the substantially non-cytotoxic composition comprises about 5 to about 1000 ppm chlorine dioxide. In another embodiment, the substantially non-cytotoxic composition comprises about 30 to about 40 ppm chlorine dioxide. In some embodiments, the substantially non-cytotoxic composition has a pH from about 4.5 to about 11. In other embodiments, the substantially non-cytotoxic composition has a pH from about 5 to about 9, or a pH greater than about 6 and less than about 8.

The substantially non-cytotoxic composition can be a thickened fluid composition comprising a thickener component in some embodiments. In some embodiments of the thickened fluid composition, the thickener component is selected from the group consisting of natural hydrocolloids, semisynthetic hydrocolloids, synthetic hydrocolloids, and clay. In an embodiment, the thickener component is a semisynthetic hydrocolloid. An exemplary semisynthetic hydrocolloid is carboxymethylcellulose, such as sodium carboxymethylcellulose.

In some embodiments, contacting the tooth with the non-cytotoxic composition does not: substantially damage hard tooth tissue, substantially reduce enamel microhardness, substantially reduce dentin microhardness, cause tooth sensitivity, and/or substantially increase surface roughness of at least one of enamel and dentin. In an embodiment, the rate and/or extent of rebound is reduced compared to a peroxide bleaching agent.

In some embodiments, the composition contacts soft oral tissue. In some embodiments, no protection of the gums is required. Optionally, in some embodiments, the composition is an oral rinse.

In some embodiments, the contacted tooth surface is whitened by at least about 3 shade value units. In other embodiments, the contacted tooth surface is whitened by at least about 6 shade value units.

In another aspect, a method of whitening a tooth surface is provided, comprising contacting the surface of a tooth with an efficacious amount of a substantially non-cytotoxic composition comprising a bleaching agent that whitens the contacted tooth surface, wherein the bleaching agent is chlorine dioxide and wherein the step of contacting the tooth surface results in substantial contact of the composition with soft oral tissues. In an embodiment, the composition is also substantially non-irritating. In some embodiments, the substantially non-cytotoxic composition comprises less than about 0.2 milligrams oxy-chlorine anion per gram composition.

In an embodiment, the substantially non-cytotoxic composition comprises about 5 to about 1000 ppm chlorine dioxide.

In another embodiment, the substantially non-cytotoxic composition comprises about 30 to about 40 ppm chlorine dioxide. In some embodiments, the substantially non-cytotoxic composition has a pH from about 4.5 to about 11. In other embodiments, the substantially non-cytotoxic composition has a pH from about 5 to about 9, or a pH greater than about 6 and less than about 8.

The substantially non-cytotoxic composition can be a thickened fluid composition comprising a thickener component in some embodiments. In some embodiments of the thickened fluid composition, the thickener component is selected from the group consisting of natural hydrocolloids, semisynthetic hydrocolloids, synthetic hydrocolloids, and clay. In an embodiment, the thickener component is a semisynthetic hydrocolloid. An exemplary semisynthetic hydrocolloid is carboxymethylcellulose, such as sodium carboxymethylcellulose.

In some embodiments, contacting the tooth with the non-cytotoxic composition does not: substantially damage hard tooth tissue, substantially reduce enamel microhardness, substantially reduce dentin microhardness, cause tooth sensitivity, and/or substantially increase surface roughness of at least one of enamel and dentin. In an embodiment, the rate and/or extent of rebound is reduced compared to a peroxide bleaching agent.

In some embodiments, no protection of the gums is required. Optionally, in some embodiments, the composition is an oral rinse. In some embodiments, the contacted tooth surface is whitened by at least about 3 shade value units. In other embodiments, the contacted tooth surface is whitened by at least about 6 shade value units.

In yet another aspect, a composition for whitening a tooth surface is provided. The composition comprises a bleaching agent and an aqueous medium, wherein the composition is substantially non-cytotoxic; the bleaching agent is chlorine dioxide; and the bleaching agent is present is an efficacious amount. In an embodiment, the composition is also substantially non-irritating. In some embodiments, the substantially non-cytotoxic composition comprises less than about 0.2 milligrams oxy-chlorine anion per gram composition.

In an embodiment, the substantially non-cytotoxic composition comprises about 5 to about 1000 ppm chlorine dioxide. In another embodiment, the substantially non-cytotoxic composition comprises about 30 to about 40 ppm chlorine dioxide. In some embodiments, the substantially non-cytotoxic composition has a pH from about 4.5 to about 11. In other embodiments, the substantially non-cytotoxic composition has a pH from about 5 to about 9, or a pH greater than about 6 and less than about 8.

The composition can be a thickened fluid composition comprising a thickener component in some embodiments. In some embodiments of the thickened fluid composition, the thickener component is selected from the group consisting of natural hydrocolloids, semisynthetic hydrocolloids, synthetic hydrocolloids, and clay. In an embodiment, the thickener component is a semisynthetic hydrocolloid. An exemplary semisynthetic hydrocolloid is carboxymethylcellulose, such as sodium carboxymethylcellulose.

In some embodiments, the composition causes substantially no decrease in enamel or dentin microhardness of a tooth. In some embodiments, the composition causes substantially no increase in surface roughness of at least one of enamel and dentin.

Also provided is a two-component whitening system. The system comprises: a first component comprising a particulate precursor of chlorine dioxide or a substantially pure chlorine dioxide solution having a neutral pH; and a second component comprising a thickener component in an aqueous medium. Combination of the first and second components yields a non-cytotoxic composition comprising an amount of chlorine dioxide efficacious for tooth whitening. The particulate precursor can comprise a metal chlorite, an acid source, and optionally a free halogen source. An exemplary metal chlorite is sodium chlorite. An exemplary acid source is sodium bisulfate. An exemplary source of a free halogen source is sodium salt of dichloroisocyanuric acid or a hydrate thereof. In an embodiment, the components of the two-component system are adapted to be admixed and applied to the teeth from a dental tray for sustained contact.

Another two-component whitening system is provided, which system comprises a first component comprising a substantially pure chlorine dioxide solution having a neutral pH; and a second component comprising a thickener component in an aqueous medium. Combination of the first and second components yields a non-cytotoxic composition comprising an amount of chlorine dioxide efficacious for tooth whitening.

BRIEF DESCRIPTION OF THE DRAWINGS

For the purpose of illustrating the various compositions and methods, there are depicted in the drawings certain embodiments of the invention. However, the compositions and their methods of use are not limited to the precise arrangements and instrumentalities of the embodiments depicted in the drawings.

FIG. 3A is the enamel of an untreated tooth. FIG. 3B is enamel surface after treatment with a non-cytotoxic $ClO_2$-containing composition. FIG. 3C is enamel surface after treatment with a professional whitening gel containing 36% hydrogen peroxide.

FIG. 4A is the dentin of an untreated tooth. FIG. 4B is dentin surface after treatment with an OTC whitening gel containing 10% hydrogen peroxide. FIG. 4C is dentin surface after treatment with a non-cytotoxic $ClO_2$-containing composition.

DETAILED DESCRIPTION

Figure 1:
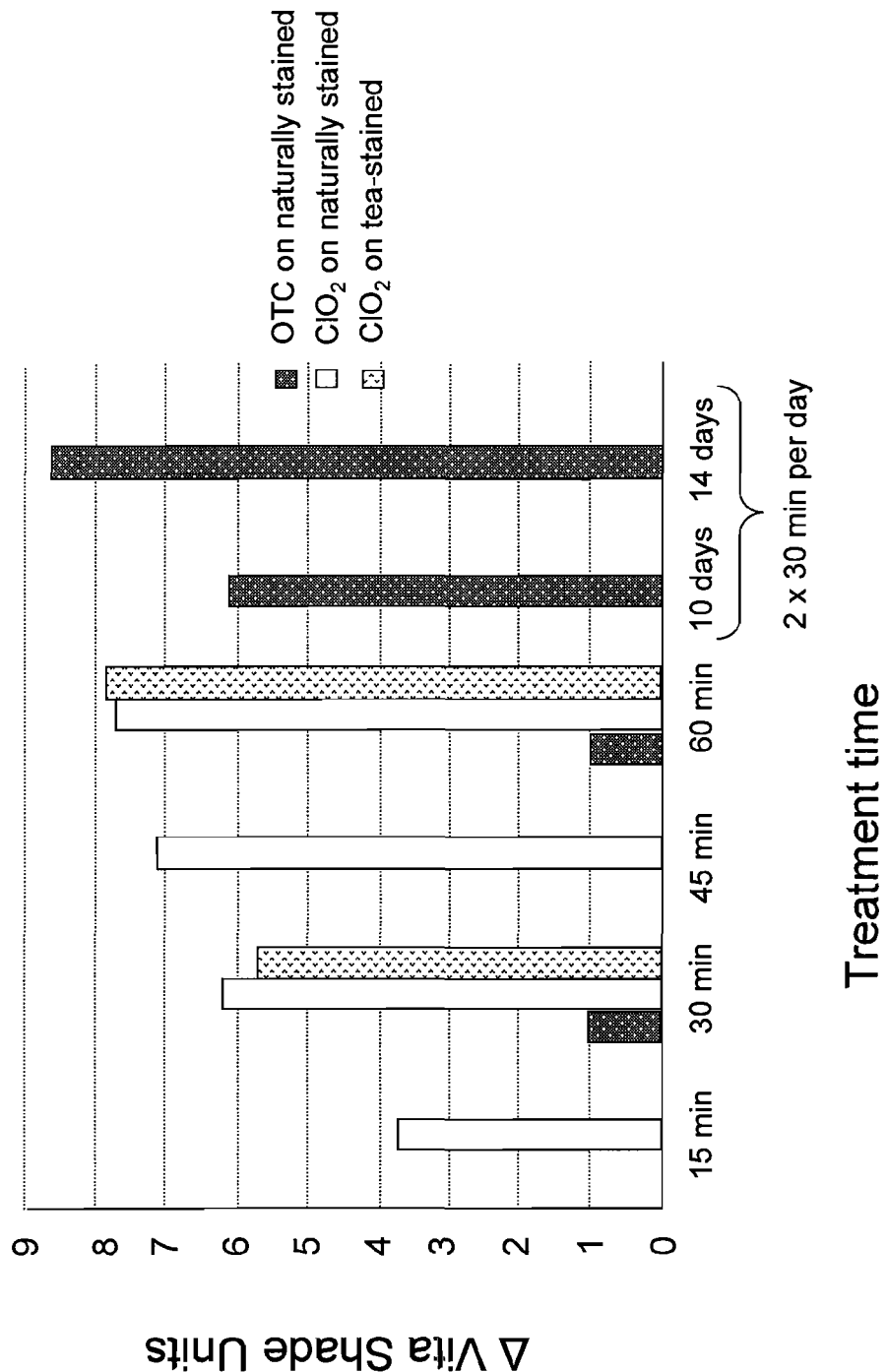
FIG. 1 is a bar graph depicting tooth whitening data for a non-cytotoxic $ClO_2$-containing composition and a commercial over-the-counter (OTC) product having 10% hydrogen peroxide as a function of total treatment time. $ClO_2$=data for non-cytotoxic $ClO_2$-containing composition. OTC=data for commercial product having 10% hydrogen peroxide.

Provided herein is a method of whitening a tooth using a composition comprising a bleaching agent, wherein the composition is not substantially cytotoxic. In a preferred embodiment, the bleaching agent can be chlorine dioxide.

DEFINITIONS

Unless defined otherwise, all technical and scientific terms used herein generally have the same meaning as commonly understood by one of ordinary skill in the art. Generally, the nomenclature used herein and the laboratory procedures in cytopathicity analysis, microbial analysis, organic and inorganic chemistry, and dental clinical research are those well known and commonly employed in the art.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it can be used. Generally, "about" encompasses a range of values that are plus/minus 10% of a reference value. For instance, "about 25%" encompasses values from 22.5% to 27.5%.

It is understood that any and all whole or partial integers between any ranges set forth herein are included herein.

As used herein, "biocidal" refers to the property of inactivating or killing pathogens, such as bacteria, algae, and fungi.

As used herein, "NaDCCA" refers to sodium dichloroisocyanurate and/or the dihydrate thereof.

As used herein, "tooth whitening" refers to a lightening of tooth shade relative to the tooth shade prior to treatment. Lightening can be assessed on an isolated or an in situ tooth by standard, art-recognized methods of assessing tooth shade, which include qualitative, quantitative and semi-quantitative methods. For instance, lightening may be assessed by simple visual inspection, e.g., by comparing "before" and "after" photographs of the treated teeth. Alternatively, a tooth may be deemed whitened when the tooth shade relative to the tooth shade prior to treatment is two or more shades lighter, as assessed by Vita classical shade guide (preferably, under controlled visible light conditions) or two or more levels as assessed using the Vita Bleachedguide 3D-MASTER Shade system, which utilizes a multiple color spectrophotometer and includes half lightness levels. A difference of one shade is referred to herein as a "shade value unit" (SVU). Thus, for example, a difference of two shades is a 2 SVU difference.

"Bleaching agent" as used herein refers to the active ingredient, or combination of ingredients, in a composition that causes the lightening and/or removal of the chromagens that contribute to the dark shade of a tooth.

As used herein, an "efficacious amount" of a bleaching agent is intended to mean any amount of a bleaching agent that will result in tooth whitening, as defined herein, using methods of assessment known to the skilled artisan, as discussed above of a tooth, with one or more treatments.

As used herein, "cytotoxic" refers to the property of causing lethal damage to mammalian cell structure or function. A composition is deemed "substantially non-cytotoxic" or "not substantially cytotoxic" if the composition meets the United States Pharmacopeia (USP) biological reactivity limits of the Agar Diffusion Test of USP <87> "Biological Reactivity, in vitro," (approved protocol current in 2007) when the active pharmaceutical ingredient (API) is present in an efficacious amount.

As used herein, "irritating" refers to the property of causing a local inflammatory response, such as reddening, swelling, itching, burning, or blistering, by immediate, prolonged, or repeated contact. A composition is deemed "substantially non-irritating" or "not substantially irritating" if the composition is judged to be slightly or not irritating using any standard method for assessing oral mucosal irritation. Non-limiting examples of such methods include: HET-CAM (hen's egg test-chorioallantoic membrane); slug mucosal irritation test; and in vitro tests using tissue-engineered oral mucosa.

As used herein, "hard tooth tissue" refers to at least one of enamel and dentin.

As used herein, "hard tooth tissue damage" refers to at least one of a reduction of microhardness of enamel, a reduction of microhardness of dentin, an increase in the surface roughness of enamel and an increase in the surface roughness of dentin.

As used herein, a composition "does not substantially damage hard tooth tissue" if one or more of the following is met for a tooth after treatment relative to the tooth prior to treatment: 1) enamel microhardness is decreased by an amount less than about 15% and/or the reduction is not statistically significant at the 5% confidence level; 2) dentin microhardness is decreased by an amount less than about 15% and/or the reduction is not statistically significant at the 5% confidence level; 3) enamel surface roughness is increased by an amount no more than about 20% and/or the increase is not statistically significant at the 5% confidence level; and 4) dentin surface roughness is increased by an amount no more than about 8% and/or the increase is not statistically significant at the 5% confidence level.

As used herein, "oxy-chlorine anion" refers to chlorite ($ClO_2^-$) and/or chlorate ($ClO_3^-$) anions.

As used herein, "substantially pure chlorine dioxide solution" refers to a solution of chlorine dioxide that has a non-cytotoxic concentration of oxy-chlorine anion. As used herein, "substantially pure chlorine dioxide solution" also refers to a concentrated solution of chlorine dioxide that contains a concentration of oxy-chlorine anion that upon dilution to an efficacious amount of chlorine dioxide is not cytotoxic with respect to the concentration of oxy-chlorine anion.

The phrase "thickened fluid composition" encompasses compositions which can flow under applied shear stress and which have an apparent viscosity when flowing that is greater than the viscosity of the corresponding aqueous chlorine dioxide solution of the same concentration. This encompasses the full spectrum of thickened fluid compositions, including: fluids that exhibit Newtonian flow (where the ratio of shear rate to shear stress is constant and viscosity is independent of shear stress), thixotropic fluids (which require a minimum yield stress to be overcome prior to flow, and which also exhibit shear thinning with sustained shear), pseudoplastic and plastic fluids (which require a minimum yield stress to be overcome prior to flow), dilantant fluid compositions (which increase in apparent viscosity with increasing shear rate), and other materials which can flow under applied yield stress.

A "thickener component," as the phrase is used herein, refers to a component that has the property of thickening a solution or mixture to which it is added. A "thickener component" can be used to make a "thickened fluid composition" as described above.

By "apparent viscosity" is meant the ratio of shear stress to shear rate at any set of shear conditions that result in flow. Apparent viscosity is independent of shear stress for Newtonian fluids and varies with shear rate for non-Newtonian fluid compositions.

The term "particulate" is used herein to refer to all solid materials. By way of a non-limiting example, particulates may be interspersed with each other to contact one another in some way. These solid materials include particles of any size, and combinations of particles of different sizes.

As used herein, "remineralization" refers to the process of repair of acid damaged tooth structure by the recrystallization of mineral salts on or within the tooth architecture.

As used herein, "demineralization" refers to the process of mineral loss from teeth caused by acid, chelating agents or other accelerants of dissolution. Demineralization can occur on tooth surfaces and/or below tooth surfaces, depending on the composition of the demineralizing agent, the contacting medium, the concentration and the pH.

DESCRIPTION

The discovery turns at least on the realization that potent and rapid tooth whitening can be achieved using chlorine dioxide compositions that are non-cytotoxic, cause minimal damage to hard tooth tissues and are substantially non-irritating to soft tissues of the mouth. As shown herein, cytotoxicity of chlorine dioxide-containing compositions results predominantly from the presence of oxy-chlorine anions, and not from the presence of chlorine, which can be a product of chlorine dioxide decomposition. Further as shown herein, substantially non-cytotoxic, non-irritating and non-hard tissue damaging compositions comprising chlorine dioxide as a bleaching agent provide rapid and extensive tooth whitening. Indeed, the rate and extent of tooth whitening achieved by such compositions were found to be superior to over-the-counter peroxide-based tooth whitening compositions and comparable to certain professional peroxide-based tooth whitening compositions. In some embodiments, the tooth surface can be whitened by at least about 3 shade value units, at least about 5 shade value units, or at least about 6 shade value units. Advantageously, substantially non-cytotoxic chlorine-dioxide containing compositions do not adversely affect enamel or dentin microhardness to a significant extent. Furthermore, the compositions do not substantially increase surface roughness of teeth, even after extended contact with the composition. Thus, tooth whitening can be obtained without substantially damaging hard tooth tissue. It is believed therefore that tooth whitening in accordance with a disclosed method will have reduced or substantially reduced tooth sensitivity and soft tissue irritation, compared to peroxide-based tooth whitening products currently available. It is further contemplated that the extent and/or rate of rebound will be reduced, compared to peroxide-based tooth whitening products currently available.

Thus, a method of whitening a tooth is provided, wherein the method comprises contacting a tooth surface with an efficacious amount of a composition, wherein the composition comprises chlorine dioxide as a bleaching agent. The composition is substantially non-cytotoxic, substantially non-irritating to soft tissues in the mouth and does not substantially damage hard tooth tissue.

I. Composition

The substantially non-cytotoxic composition used in the practice of the method is an aqueous fluid that comprises chlorine dioxide, or the reactants for generating chlorine dioxide, as a bleaching agent. In preferred embodiments, the composition comprises a thickener component which renders the composition a thickened aqueous fluid. In another preferred embodiment, the composition can be an oral rinse that may be held in the mouth in contact with teeth, as well as soft tissue.

Compositions useful in the practice of the method comprise at least about 5 ppm chlorine dioxide, preferably at least about 20 ppm, and more preferably at least about 30 ppm. Typically, the amount of chlorine dioxide can be up to about 1000 ppm, preferably up to about 700 ppm, more preferably up to about 500 ppm and more preferably still up to about 200 ppm. In certain embodiments, the chlorine dioxide concentration ranges from about 5 to about 700 ppm, preferably from about 20 to about 500 ppm, and most preferably from about 30 to about 200 ppm chlorine dioxide. In one embodiment, the composition comprises about 30 to about 40 ppm chlorine dioxide. In one embodiment, the composition comprises about 30 ppm. In another embodiment, the composition comprises about 40 ppm.

Soft tissue irritation can result from highly reactive oxygen species, such as those found in peroxide based compositions. Soft tissue irritation can also result from extremes of pH, both acidic and basic. To minimize soft tissue irritation of the chlorine dioxide containing composition, the substantially non-cytotoxic composition has a pH of at least about 3.5. To minimize possible hard surface erosion, the composition has a pH of at least about 4.5. Preferably, the composition has a pH of at least about 5, and more preferably still, greater than about 6. In certain embodiments, the pH ranges from about 4.5 to about 11, more preferably from about 5 to about 9, and more preferably still, greater than about 6 and less than about 8. In one embodiment, the pH is about 6.5 to about 7.5. Irritation is not believed to result from the concentration of oxy-chlorine anions.

For compositions comprising chlorine dioxide, as shown herein, cytotoxicity results predominantly from the presence of oxy-chlorine anions. Accordingly, a composition comprising chlorine dioxide that comprises zero milligram (mg) oxy-chlorine anion per gram composition to no more than about 0.25 mg oxy-chlorine anion per gram composition, preferably zero to about 0.24, 0.23, 0.22, 0.21, or 0.20 mg oxy-chlorine anion per gram composition, more preferably zero to about 0.19, 0.18, 0.17, 0.16, 0.15, 0.14, 0.13, 0.12, 0.11, or 0.10 mg oxy-chlorine anion per gram composition and more preferably still from zero to about 0.09, 0.08, 0.07, 0.06, 0.05 or 0.04 mg oxy-chlorine anion per gram composition, absent other constituents that contribute to cytotoxicity, is substantially non-cytotoxic.

A substantially non-cytotoxic composition comprising chlorine dioxide can be prepared using a substantially pure chlorine dioxide solution having a neutral pH. Preferably, the solution has a pH from about 5 to about 9, and more preferably, from about 6.5 to about 7.5. One source of a substantially pure chlorine dioxide solution can be chlorine dioxide is prepared using an ASEPTROL (BASF Corp., Florham Park, N.J.) material, which are described in commonly-assigned U.S. Pat. Nos. 6,432,322 and 6,699,404. These patents disclose solid bodies for preparing highly converted solutions of chlorine dioxide when added to water. The solid body comprises a metal chlorite such as sodium chlorite, an acid source such as sodium bisulfate and optionally a source of free halogen such as the sodium salt of dichloroisocyanuric acid or a hydrate thereof. ASEPTROL materials provide a way to efficiently generate chlorine dioxide at substantially neutral pH, thus avoiding tooth-compatibility problems existing with earlier, acidic chlorine dioxide based oral products. ASEPTROL material in an aqueous fluid has an extremely high conversion rate, resulting in high concentrations of chlorine dioxide and low concentrations of oxy-chlorine anion.

Another method of preparing substantially pure chlorine dioxide can be to prepare a chlorine dioxide source solution by any known method, then bubbling air through that solution (sparging) and into a second container of deionized water, to prepare the product solution of substantially pure chlorine dioxide. Only $ClO_2$ and possibly some water vapor is transferred from the source solution to the product solution. All the salt ingredients remain behind in the source solution. Thus, there are no oxy-chlorine anions in the substantially pure product solution. While the chlorine dioxide may undergo a degree of decomposition, the rate is relatively slow. By keeping the solution capped and protected from ultraviolet exposure, the decomposition rate can be slowed to a rate of about 5 to about 25% reduction in chlorine dioxide in 7 days. Substantially pure chlorine dioxide may also be prepared using a pervaporation technique, such as that disclosed in U.S. Pat. No. 4,683,039. In addition, a metal chlorite and an acid source can be reacted in solution to yield high conversion to chlorine dioxide and produce a greater than 2000 ppm chlorine dioxide solution. The concentrated solution can then be buffered to a neutral pH. Similarly, a chlorine dioxide solution can be prepared the composition described in U.S. Pat. No. 5,399,288, which yields a high concentration chlorine dioxide solution at acidic pH. The concentrated solution can then be buffered to achieve a substantially neutral pH to prepare a substantially pure chlorine dioxide solution.

Oxy-chlorine anions can be measured in these solutions using any method known to those skilled in the art, including ion chromatography following the general procedures of EPA test method 300 (Pfaff, 1993, "Method 300.0 Determination of Inorganic Anions by Ion Chromatography," Rev. 2.1, US Environmental Protection Agency) or a titration method based on an amperometric method (Amperometric Method II in Eaton et al, ed., "Standard Methods for the Examination of Water and Wastewater" $19^{th}$ edition, American Public Health Association, Washington D.C., 1995). Alternatively, oxy-chlorine anions may be measured by a titration technique equivalent to the amperometric method, but which uses the oxidation of iodide to iodine and subsequent titration with sodium thiosulfate to a starch endpoint in place of the amperometric titration; this method is referred to herein as "pH 7 buffered titration." A chlorite analytical standard can be prepared from technical grade solid sodium chlorite, which is generally assumed to comprise about 80% by weight of pure sodium chlorite.

To prepare a thickened aqueous composition comprising chlorine dioxide that is substantially not cytotoxic, non-irritating and does not damage hard tooth tissue, the substantially pure chlorine dioxide solution can then be combined with a thickener component and an aqueous medium. The materials and methods also encompass a two-component whitening system comprising a first component comprising a substantially pure chlorine dioxide solution and a second component comprising a thickener component in an aqueous medium. Combination of the first and second components yields a non-cytotoxic composition comprising an amount of chlorine dioxide efficacious for tooth whitening. Chlorine dioxide in solution will decompose over time. To avoid problems arising from such decomposition, including loss of efficacy and generation of chlorite anions, the substantially pure chlorine dioxide solution can be prepared immediately before its combination with a thickener component and an aqueous medium. In addition, the composition can be prepared immediately before its use.

"Immediately before" as used herein refers to a period no greater than that which would result in diminished efficacy or evidence of cytotoxicity. Generally, "immediately before" is less than about 14 days, and preferably no greater than about 24 hours and more preferably no greater than about 2 hours. Preferably, the substantially pure chlorine dioxide solution is prepared within about 8 hours of the preparation of the composition. Precautions are also taken to avoid exposing the chlorine dioxide solution or the prepared composition to strong ultraviolet light or elevated temperature (e.g., temperature greater than ambient temperature, about 25° C.).

Methods of preparing substantially non-cytotoxic thickened compositions comprising chlorine dioxide are also disclosed in commonly-assigned U.S. provisional application No. 61/150,685, filed Feb. 6, 2009, entitled "Non-Cytotoxic Chlorine Dioxide Fluids," incorporated herein by reference in its entirety.

Methods of preparing thickened compositions comprising chlorine dioxide are also disclosed in commonly-assigned U.S. Pat. Publication Nos. 2006/0169949 and 2007/0172412. In practicing the methods described in these two publications, steps must be taken (as described herein) to control the oxychlorine concentration so as to produce a non-cytotoxic composition.

A substantially non-cytotoxic composition comprising chlorine dioxide can also be prepared using a particulate precursor of $ClO_2$ and an aqueous thickened fluid composition. Another aspect encompasses a two-component whitening comprising a first component comprising a particulate precursor of chlorine dioxide and a second component comprising a thickener component in an aqueous medium. Combination of the first and second components yields a non-cytotoxic composition comprising an amount of chlorine dioxide efficacious for tooth whitening. In an embodiment, the components of the system are adapted to be admixed and applied to the teeth from a dental tray for sustained contact. Precursors of $ClO_2$ include metal chlorites, metal chlorates, an acid source and an optional halogen source. The particulate precursor may comprise one of these or any combination of these. The particulate precursor can be an ASEPTROL product, more preferably it can be ASEPTROL S-Tab2. ASEPTROL S-Tab2 has the following chemical composition by weight (%): $NaClO_2$ (7%); $NaHSO_4$ (12%); NaDCC (1%); NaCl (40%); $MgCl_2$ (40%). Example 4 of U.S. Pat. No. 6,432,322 describes an exemplary manufacture process of S-Tab2. Granules can be produced, either by comminuting pressed S-Tab2 tablets, or by dry roller compaction of the non-pressed powder of the S-Tab2 components, followed by breakup of the resultant compacted ribbon or briquettes, and then screening to obtain the desired size granule. Upon exposure to water or an aqueous thickened fluid, chlorine dioxide can be generated from the ASEPTROL granules. In one embodiment, a substantially non-cytotoxic composition comprising chlorine dioxide can be prepared by combining −40 mesh granules with an aqueous thickened fluid. In one aspect, the thickener component of the thickened fluid can be carboxymethylcellulose (CMC). Preferably, the aqueous thickened fluid can be prepared sufficiently in advance of combining with the ASEPTROL granules to enable the complete hydration of the thickener component. In one embodiment, the thickened fluid composition is formed by adding high viscosity NaCMC powder to distilled water. The NaCMC is allowed to hydrate for at least 8 hours, and then the mixture is stirred to homogenize it. A substantially non-cytotoxic composition for tooth whitening is then prepared by mixing the sized ASEPTROL granules with the NaCMC thickened fluid composition.

The thickened fluid composition may also be formed in situ, wherein saliva serves as the aqueous medium. In one embodiment, a mixture of ASEPTROL granules and a thickener component can be formed into a shape, for instance by addition of a malleable wax, and the shape is then applied to teeth. Saliva activates the granules, forming chlorine dioxide and the thickener component hydrates, thereby forming the thickened fluid composition in situ. In another embodiment, a mixture of ASEPTROL granules and a thickener component can be placed on a dental strip or a dental film or in a dental tray. A dental strip refers to a substantially planar object made of a plastic backbone that is sufficiently flexible to affix to teeth. A dental film refers to a substantially planar object made of a pliable, conformable material that can be substantially fitted to the surface of teeth. Optionally, the dental strip is dissolvable in an aqueous medium, such as saliva. The strip, film or tray can be positioned on teeth, and saliva serves as the aqueous medium as described above to produce the thickened fluid composition in situ. Alternatively, the mixture on the strip or tray can be contacted with water or aqueous medium prior to positioning on the teeth.

There is no extremely accurate method for measuring oxy-chlorine anion directly in a thickened fluid composition. This value can be accurately estimated, however, by measuring the oxy-chlorine anion in the aqueous solution (prior to thickening), and adjusting the final concentration on the basis of weight of the final thickened fluid. The titration method described elsewhere herein is contemplated as useful in assessing both the chlorine dioxide concentration and the oxy-chlorine anion concentration in thickened fluid compositions. It is contemplated that oxy-chlorine anions in a thickened fluid composition can be measured using ion chromatography as described elsewhere herein, provided steps are taken to preclude fouling of the column by the hydrated thickener component. One such step is the use of molecular weight filters to remove the hydrated thickener component, such as hydrated CMC, prior to application to the chromatography column. If necessary, the thickened fluid composition may be diluted with water, prior to analysis, to reduce its viscosity or otherwise allow it to be more readily tested. One of skill in the art can readily determine empirically whether a given formulation has a sufficiently low oxy-chlorine concentration by determining if the formulation is cytotoxic using USP biological reactivity limits of the Agar Diffusion Test of USP <87>.

The aqueous thickened fluid composition used in the method may comprise any thickener component in an aqueous medium, wherein the thickened fluid composition can be non-cytotoxic and non-irritating to soft tissues, in particular oral mucosa, and causes minimal damage to hard tissues, such as tooth enamel and dentin. In addition, the thickener is preferably not adversely affected by the bleaching agent on the time scale of composition preparation and use in treatment. Many thickener agents are known in the art, including, but not limited to carbomers (e.g., CARBOPOL thickeners, Lubrizol Corp., Wickliffe, Ohio), carboxymethylcellulose (CMC), ethylcellulose, hydroxyethylcellulose, hydroxypropyl cellulose, natural smectite clays (e.g., VEEGEM, R. T. Vanderbilt Co., Norwalk, Conn.), synthetic clays (e.g., LAPONITE (Southern Clay Products, Gonzales, Tex.), methylcellulose, superabsorbent polymers such as polyacrylates (e.g., LUQUASORB 1010, BASF, Florham Park, N.J.), poloxamers (PLURONIC, BASF, Florham Park, N.J.), polyvinyl alcohol, sodium alginate, tragacanth, and xanthan gum. Such thickening agents may be categorized into four groups: natural hydrocolloids (also referred to as "gum"), semisynthetic hydrocolloids, synthetic hydrocolloids, and clay. Some examples of natural hydrocolloids include acacia, tragacanth, alginic acid, carrageenan, locust bean gum, guar gum, and gelatin. Non-limiting examples of semisynthetic hydrocolloids include methylcellulose and sodium carboxymethylcellulose. Some examples of synthetic hydrocolloids (also referred to as "polymers" including polymers, cross-linked polymers, and copolymers) include polyacrylates, superabsorbent polymers, high molecular weight polyethylene glycols and polypropylene glycols, polyethylene oxides and CARBOPOL. Non-limiting examples of clay (including swelling clay) include LAPONITE, attapulgite, bentonite and VEEGUM. An exemplary thickener component is a semi-synthetic hydrocolloid. Another exemplary thickener component can be a high viscosity sodium carboxymethylcellulose (NaCMC powder).

CMC is a cellulose derivative with carboxymethyl groups ($-CH_2-COOH$) bound to some of the hydroxyl groups of the glucopyranose monomers that make up the cellulose backbone. It can be synthesized by the alkali-catalyzed reaction of cellulose with chloroacetic acid. The polar (organic acid) carboxyl groups render the cellulose soluble and chemically reactive. The functional properties of CMC depend on the degree of substitution of the cellulose structure (i.e., how many of the hydroxyl groups have taken part in the substitution reaction), and chain length of the cellulose backbone structure.

CMC is available in a range of viscosity grades and to USP standards. High viscosity CMC, such as type CA194 from Spectrum Chemical Manufacturing Company, has a viscosity of between 1500 and 3000 cps at 25° C. at 1% concentration in water.

The composition can be a fluid. In some embodiments, the fluid can be a thickened fluid having flow properties suitable for applying the fluid to a tooth surface and leaving the fluid in place for the duration of a tooth whitening treatment (e.g., about 5 to about 60 minutes). Accordingly, a pseudoplastic composition with a sufficient yield point to retains its shape when applied to teeth but low enough to be readily removed by wiping is advantageous in practicing the method. In embodiments where the composition is contacted to a tooth using a dental tray, strip, or similar device, the composition should have sufficient adhesion to hold the device in place. Exemplary adhesion agents are disclosed in U.S. Pat. Publication No. 2008/0025925.

The composition may optionally comprise other components. Such components include, but are not limited to, sweeteners, flavorants, coloring agents, and fragrances. Sweeteners include sugar alcohols. Exemplary sugar alcohols include sorbital, xylitol, lactitol, mannitol, maltilol, hydrogenated starch hydrolysate, erythritol, reducing paratinose, and mixtures thereof. Flavoring agents include, e.g., natural or synthetic essential oils, as well as various flavoring aldehydes, esters, alcohols, and other materials. Examples of essential oils include oils of spearmint, peppermint, wintergreen, sassafras, clove, sage, eucalyptus, marjoram, cinnamon, lemon, lime, grapefruit, and orange. Coloring agents include a colorant approved for incorporation into a food, drug, or cosmetic by a regulatory agency, such as, for example, FD&C or D&C pigments and dyes approved by the FDA for use in the United States. Fragrances include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA), and the like.

Other optional components for the composition include: antibacterial agents (in addition to chlorine dioxide), enzymes, malodor controlling agents (in addition to chlorine dioxide), cleaning agents, such as phosphates, antigingivitis agents, antiplaque agents, antitartar agents, anticaries agents, such as a source of fluoride ion, antiperiodontitis agents, nutrients, antioxidants, and the like. Advantageously, the method can reduce or eliminate the need for agents to relieve tooth sensitivity and agents for remineralizing the enamel. However, such agents may be included in the composition in some embodiments. Exemplary agents are well-known in the art. See e.g., U.S. Pat. Publication Nos. 2005/0287084; 2006/0263306; 2007/0259011; and 2008/0044363.

It is preferred that all optional components are relatively resistant to oxidation by chlorine dioxide, since oxidation of composition components by chlorine dioxide will reduce the available chlorine dioxide for oxidation of chromagens on a tooth. "Relatively resistant" means that in the time scale of preparing and using the chlorine dioxide-containing composition, the function of the optional component is not diminished, and the composition retains tooth whitening efficacy and remains substantially non-cytotoxic, substantially non-irritating, and does not substantially damage hard tooth tissue.

II. Method of Use

The method can be practiced by contacting a tooth surface with a substantially non-cytotoxic composition comprising a bleaching agent in an efficacious amount. Advantageously, no pre-treatment of the gums is required, because the composition is substantially non-irritating and substantially non-cytotoxic. The duration of contact with the tooth to achieve a measurable degree of tooth whitening can be readily determined by the skilled artisan in view of the teachings herein. Advantageously, even after prolonged contact, the composition does not substantially damage hard tooth tissue. Generally, duration of contact ranges from seconds to minutes, preferably at least about 60 seconds, more preferably at least about 1, 2, 3, 4, or 5 minutes, still more preferably about 6, 7, 8, 9, or 10 minutes, yet more preferably about 11, 12, 13, 14, or 15 minutes, though contact can range up to 16, 17, 18, 19, or 20 minutes, and further up to 21, 22, 23, 24, 25, 26, 27, 28, 29, or 30 minutes, and further up to about 35, 40, 45, 50, 55, or 60 minutes or longer in some circumstances. In certain embodiments, duration of contact ranges between about 1 and about 60 minutes, more preferably, from about 5 minutes to about 30 minutes, and more preferably still, about 10 to about 20 minutes. In a preferred embodiment, duration of contact for a treatment is about 15 minutes. Treatment frequency is also readily determined by skilled artisan armed with the present disclosure. Treatment may comprise one episode of tooth contact or more than one episode. Treatment episodes may be contiguous, separated in time (e.g., a few hours to a few days, a few days to a few weeks, and also longer intervals including several months to a year or more) or both.

Contact between the composition and the tooth surface can be achieved by any of a number of well-known methods in the art. The composition can be brushed or spread onto the tooth surface. The composition can be present on a flexible strip or patch that can be pressed against and molded to the tooth surface. The composition can be used as an oral rinse; accordingly, the composition can be held in the mouth and allowed to contact the teeth either statically, or with agitation within the mouth using, for example, the tongue and cheeks. The composition can be placed in a dental tray, which is then placed in contact with the teeth. Such trays may be custom made or non-custom made. Numerous devices useful in practicing the methods and using the compositions are disclosed in the art including, but not limited to U.S. Pat. Nos. 5,879,691; 6,551,579; 6,682,721; 6,848,905; 6,896,518; 6,964,571; 7,004,756; 7,040,897; and U.S. Pat. Publication Nos. 2006/0223033; 2007/0298380; and 2008/0025925.

In some embodiments, the method can be practiced using a dental tray. The tray can be custom made. Methods of making custom-made trays are well known in the art; see, for instance, U.S. Pat. Nos. 6,106,284 and 6,425,759, and US Pat. Publication Nos. 2006/0183080 and 2008/0041400. In brief, an impression tray can be filled with an impression material, such as alginate. The impression tray can then be positioned into the mouth of the patient so as to create a negative impression of the teeth in the impression material. After the negative impression has been formed, the negative impression created in the impression tray can be filled with a soft casting material, such as dental stone, plaster or epoxy. The impression tray can be then inverted and mounted upon a pre-formed mounting device, such as a dental cast tray or base. After the casting material has had an opportunity to harden, the impression tray is removed so that the casting material forms a positive dental impression on the mounting surface. Another method of preparing a custom dental tray makes use of a "boil and bite" material, which is made out of a thermoformable plastic such as ethyl vinyl acetate ("EVA") or polyethylene. A customized tray can be created by heating the thermoformable plastic in boiling water causing it to melt at a biologically acceptable temperature, and then placing it directly over an individual's teeth where it cools and retains its new shape. To practice a method, the substantially non-cytotoxic composition comprising a bleaching agent can be placed into the dental tray. The tray is then positioned in the patient's mouth for the treatment episode.

It is also contemplated that administration of a chlorine dioxide composition may be made substantially non-cytotoxic by minimizing or precluding contact of soft tissues with oxy-chlorine anions present in the composition. Accordingly, as an example, devices comprising a microporous barrier permeable to chlorine dioxide and substantially non-permeable to oxy-chlorine anions are envisioned. The chlorine dioxide composition may be completely or partially enclosed by such a selectively-permeable barrier. In some embodiments, the membrane can be hydrophobic; the hydrophobic nature of the membrane prevents both an aqueous reaction medium and an aqueous recipient medium from passing through the membrane. Features to consider for the materials used for such a barrier include: hydrophobicity of the microporous material, pore size, thickness, and chemical stability towards the attack of chlorine dioxide, chlorine, chlorite, chlorate, chloride, acid and base. Of course, for contact with soft tissues, the microporous barrier should be substantially non-irritating and substantially non-cytotoxic, particularly in the time scale of typical use of the device. It is envisioned that the chlorine dioxide composition utilized in such a device need not be a thickened fluid, provided the device can be affixed to the tooth surface, and enable the chlorine dioxide that permeates through the membrane to contact the tooth surface.

Materials useful as such barriers are known in the art and include expanded polytetrafluoroethylene (e.g., GORE-TEX) and polyvinylidenefluoride (PVDF). See, for instance, U.S. Pat. No. 4,683,039. The procedure for formation of a expanded polytetrafluoroethylene is described in U.S. Pat. No. 3,953,566. The material may be provided as a composite with supporting materials to provide the structural strength required for use.

The pore sizes in the barrier may vary widely, depending on the desired flow rate of the chlorine dioxide through the barrier. The pores should not be so small as to prevent chlorine dioxide gas flow therethrough but also should not be so large that liquid flow is permitted.

The porosity of the barrier may vary widely, also depending upon the desired flow rate of chlorine dioxide through the barrier. Considerations of barrier strength also dictate the porosity chosen. Generally, the barrier porosity varies from about 50 to about 98%.

Also contemplated is the use of reactants for the formation of $ClO_2$ embedded in a polymeric material that is permeable to $ClO_2$ but substantially non-permeable to oxy-chlorine anions. See e.g., U.S. Pat. No. 7,273,567.

As shown herein, a substantially non-cytotoxic composition comprising chlorine dioxide as a bleaching agent has unexpected robust whitening capacity. Furthermore, a substantially non-cytotoxic composition comprising chlorine dioxide causes minimal damage to hard surfaces, such as enamel and dentin, even during extended contact with an efficacious amount on a tooth surface. In some embodiments, microhardness of enamel contacted by a substantially non-cytotoxic composition is decreased less than about 15%, and preferably less than about 10%, less than about 8% and more preferably still, less than about 5%, relative to the enamel prior to contact. In some embodiments, enamel microhardness can be decreased less than about 1% after a total treatment time of about seven (7) hours, relative to the enamel prior to contact. In some embodiments, microhardness of dentin contacted by a substantially non-cytotoxic composition is decreased less than about 15%, or less than about 10%, and or even less than about 8%, relative to the enamel prior to contact. In some embodiments, dentin microhardness can be decreased less than about 8% after a total treatment time of about seven (7) hours, relative to the dentin prior to contact. Enamel and dentin surface roughness are also not substantially increased by contact with a substantially non-cytotoxic composition. Preferably, surface roughness is increased by no more than about 20%, more preferably no more than about 15%, more preferably no more than about 10%, and more preferably still, no more than about 8%, relative to the surface roughness prior to contact.

Thus, as shown herein, a substantially non-cytotoxic chlorine dioxide-comprising composition advantageously provides a high degree of tooth whitening rapidly, with substantially no damage to hard tooth tissue, no irritation of soft mucosal tissue, and no tooth sensitivity. This is in marked contrast to currently-available products based on hydrogen peroxide, which are cytotoxic and an irritant to soft tissues and frequently cause tooth sensitivity and demineralization. For instance, professional tooth lightening hydrogen peroxide products require steps prior to treatment to protect the gums during treatment. Both over-the-counter and professional hydrogen peroxide-based products often cause undesirable side effects, including pain, sensitivity and irritation of soft and/or hard tissues. Additionally, the use of a non-cytotoxic chlorine dioxide-comprising composition has minimal adverse effect on enamel and dentin microhardness and surface roughness. This combination of highly effective tooth lightening coupled with minimal unpleasant side effects is very desirable, and not achieved in prior art efforts. The method does not require the use of an external activator, such as a bleaching light or laser, and tooth whitening equal or superior to current over-the-counter bleaching materials may be obtained in less overall treatment time. In addition, tooth whitening equal or superior to current professional bleaching materials can be obtained without cytotoxicity and irritation of soft tissue. In particular, the absence of soft tissue irritation advantageously permits the dental professional to proceed without a gum-protection step, which can take as long as about 90 minutes. Indeed, substantial contact with soft oral tissue can be possible without irritation or cytotoxicity. "Substantial contact with soft oral tissue" as used herein refers to contact that is more than contact with gum tissue proximal to a treated tooth. Thus, substantial contact includes, but is not limited to, contact with gum, cheek mucosal and tongue tissue. Furthermore, the minimal effect on enamel and dentin microhardness reduces or eliminates the need for tooth sensitivity treatment and/or a remineralization procedure, both of which are often required with hydrogen peroxide-based tooth lightening products. In addition, it has been suggested that the increased surface roughness observed after hydrogen peroxide bleaching provides an increased surface, which may facilitate early restaining after whitening treatment. The method advantageously does not increase surface roughness. Accordingly, it is contemplated that the method will also provide a reduced rate and/or extent of rebound after whitening.

Chlorine dioxide slowly decays over time. Thus, when the method can be practiced using a composition comprising chlorine dioxide, to maximize the tooth whitening potency of the composition and to assure non-cytotoxicity, the composition can be prepared immediately before use or is prepared in situ, as described elsewhere herein. Preparation can be accomplished by methods described in commonly-assigned U.S. provisional application No. 61/150,685, filed Feb. 6, 2009, entitled "Non-Cytotoxic Chlorine Dioxide Fluids."

In a preferred embodiment, a particulate precursor of chlorine dioxide is present in a first dispenser, such as a syringe, and a thickener component in an aqueous medium is present in a second dispenser. The aqueous thickened fluid in the second dispenser can be added directly to the particulate mixture in the first dispenser, the combination allowed to react to produce $ClO_2$, and then mixed until homogeneous. Alternatively, an aqueous medium can be added to the particulate precursor to prepare a substantially pure chlorine dioxide solution. The appropriate amount of this solution can be then mixed with the aqueous thickener in the other dispenser. Both these embodiments are advantageously practiced using syringes as the dispenser. In either embodiment, the two syringes can be connected to each other, and the contents combined by dispensing the contents of one syringe into the other, then dispensing the mixture back into the other syringe until the mixture is homogeneous. In another embodiment, the two dispensers are the two barrels of a dual barrel syringe. Other devices to prepare and dispense the composition are described in commonly-assigned U.S. provisional application No. 61/150,685, filed Feb. 6, 2009, entitled "Non-Cytotoxic Chlorine Dioxide Fluids."

III. Kits and Other Articles of Manufacture

Also provided herein is a kit comprising the composition, or the ingredients therefore, and an instructional material, which describes using the composition in a method of whitening a tooth. As used herein, an "instructional material," includes a publication, a recording, a diagram, or any other medium of expression that can be used to communicate the usefulness of the composition and/or compound in a kit. The instructional material of the kit may, for example, be affixed to a container that contains the compound and/or composition or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

In an embodiment, the kit comprises two dispensers useful for preparing the composition. One dispenser comprises a particulate precursor of chlorine dioxide. The second dispenser comprises a thickener component in an aqueous medium.

In another embodiment, the kit comprises a two-compartment container. One compartment comprises a particulate precursor of chlorine dioxide. The second compartment can comprise a thickener component in an aqueous medium.

Optionally, the container comprises a third compartment for combining some or all of the contents of the two other compartments.

In some embodiments of the kit, the particulate precursor is ASEPTROL granules, preferably ASEPTROL S-Tab2 granules. In some embodiments of the kit, the thickener component can be CMC. In preferred embodiments of the kit, the particulate precursor comprises ASEPTROL S-Tab2 granules and the thickener component comprises CMC.

Optionally, the kit further comprises an applicator. By the term "applicator," as the term is used herein, is meant any device including, but not limited to, a dental tray, a syringe, a pipette, a brush, a cup, and the like, suitable for contacting the tooth surface with the composition.

EXAMPLES

The compositions and methods of use are further described in detail by reference to the following experimental examples. These examples are provided for purposes of illustration only, and are not intended to be limiting unless otherwise specified. Thus, the compositions, methods of use, and kits should in no way be construed as being limited to the following examples, but rather, should be construed to encompass any and all variations which become evident as a result of the teaching provided herein.

Experimental Example 1

Cytotoxicity Analysis

To test the effects of chlorine dioxide on mammalian cells, the following experiment was performed. Two series of samples comprising different amounts of chlorite anion were prepared. Examples 1-4 used a super absorbent polyacrylate gel (labeled gel type "S"). Examples 5-8 used a carboxymethylcellulose (CMC) gel (labeled gel type "C").

ASEPTROL S-Tab2 granules were used in the gel compositions used in this experiment. The chemical composition of the granules is shown in Table 1.

TABLE 1

| Component | % (wt/wt) |
|---|---|
| Sodium chlorite | 7% |
| Dichloroisocyanuric acid, sodium salt | 1% |
| Sodium bisulfate | 12% |
| Sodium chloride | 40% |
| Magnesium chloride | 40% |

Sodium chlorite (Aragonesas Energia of Spain) was technical grade, containing nominally 80% (0.8) by weight $NaClO_2$ and 20% inorganic stabilizer salts such as NaCl, NaOH, $Na_2CO_3$, and $Na_2SO_4$. Dichloroisocyanuric acid sodium salt ($NaCl_2(CNO)_3 \cdot 2H_2O$) was obtained from Oxychem as ACL-56.

The tablets, from which granules were made, were prepared as essentially as described in Example 4 of U.S. Pat. No. 6,432,322, incorporated herein by reference. In brief, each of the separate components of the granules was dried. The appropriate quantities of the components were mixed together and the mixture was compacted into tablet form using a hydraulic table press. The thus-formed tablets were ground into granules using a mortar and pestle. The resultant granules were screened using a 40 mesh US Standard screen; the −40 mesh size fraction was used in the experiments.

ASEPTROL S-Tab2 tablets have a high degree of conversion of chlorite anions to $ClO_2$ (see Examples in U.S. Pat. No. 6,432,322). Typically, a solution made from such tables will contain about 10× as much $ClO_2$ as residual chlorite anion. When contacted with water (liquid), the water is absorbed into the pores of the tablet, where it forms a saturated aqueous solution of the constituents. Such conditions (high concentration of chlorite anion and low pH) are advantageous for the reaction of chlorite anion ($ClO_2^-$) with acid or chlorine to produce chlorine dioxide ($ClO_2$) by reactions:

$$5NaClO_2 + 4H^+ \rightarrow 4ClO_2 + NaCl + 4Na^+ + 2H_2O \qquad \text{Eq. 3}$$

$$2NaClO_2 + OCl^- + H^+ \rightarrow 2ClO_2 + NaCl + NaOH \qquad \text{Eq. 4}$$

Residual chlorite anion in solution can result from several sources. A source of residual chlorite anion in solution is sodium chlorite, which dissolves from the exterior surface of an ASEPTROL tablet (or granule) into the bulk solution. The conversion rate of chlorite anion to $ClO_2$ is low at the very dilute and generally neutral-pH conditions of the bulk solution, so any chlorite anion that dissolves from the exterior of a tablet or granule will remain substantially unconverted and remain as chlorite anion in solution. As a result, anything that enhances surface dissolution of sodium chlorite prior to its conversion to $ClO_2$ will result in an increase in chlorite anion concentration in the resultant solution or gel.

Each base gel (aqueous thickened fluid) was slightly different to compensate for the different active ingredient concentrations in the final samples. The final concentration of thickener component in the prepared gel samples was the same within each series. Each sample was made in an about 30 gram amount. The base gels were prepared by combining deionized water with the gelling agents (thickener component). To allow the gelling agents to become fully hydrated, the mixtures were allowed to stand for several hours to overnight. The base gel mixtures were then stirred to homogenize the base gel.

The samples were prepared by combining ASEPTROL granules with a base gel shortly before use. The exposure of the ASEPTROL material to ambient humidity or water was minimized prior to use to avoid loss of potency. After ASEPTROL granules were added to the base gel, the samples were mixed for 30 seconds with a stainless steel or plastic spatula, capped and left to stand at room temperature for 5 minutes. The samples were then mixed a second time for 30 seconds to homogenize the sample. Prepared samples were tightly capped until time of testing. The sodium chlorite granules and the prepared samples were protected from strong uv lights to limit uv-induced decomposition. Testing was begun no more than 2 hours after the samples were prepared.

Chlorine dioxide concentration was assessed by pH 7 buffered titration using potassium iodide (KI) and sodium thiosulfate on other samples. Samples 1 and 5 had zero chlorine dioxide. Samples 2 and 6 had about 30 ppm $ClO_2$. Samples 3 and 7 had about 40 ppm and samples 4 and 8 had about 580 ppm $ClO_2$ There is not an extremely accurate method for measuring directly chlorite anions in a thickened fluid composition. Thus, the maximum concentration of chlorite anion possibly present in each prepared sample is provided below. It is expected that the actual amount of chlorite anion is less the maximum, as the reactants are activated in the presence of an aqueous medium and generate chlorine dioxide, thus consuming chlorite anions. The maximum amount of chlorite anion possibly present in a sample was calculated using the following formula:

((wt. S_tab2 granules×wt. fraction sodium chlorite in granules×wt. fraction chlorite in sodium chlorite×nominal wt. fraction of sodium chlorite)× 1000)/total wt of final sample.

The weight fraction of sodium chlorite used in S-Tab2 granules is 0.07. The weight fraction of chlorite in sodium chlorite is 0.74. The nominal weight fraction of actual sodium chlorite in the sodium chlorite powder (i.e., the purity of the sodium chlorite) used in the granules is 0.8. Thus, for instance, the calculation of the milligrams of oxy-chlorine anion per gram of gel for Ex. 2 is:

((0.143 g.×0.07×0.74×0.8)×1000)/30 grams final sample.

The final formulation for the examples is shown in Tables 2 and 3.

TABLE 2

| Component | Sample 1 | Sample 2 | Sample 3 | Sample 4 |
|---|---|---|---|---|
| Sodium polyacrylate[1] | 1.4 | 1.4 | 1.4 | 1.4 |
| NaCl | 1 | 1 | 1 | 0 |
| Polyethylene oxide[2] | 1.6 | 1.6 | 1.6 | 1.6 |
| Deionized water | 26 | 25.9 | 25.6 | 25.6 |
| S-Tab2 granules (−40 mesh) | 0 | 0.143 | 0.357 | 1.43 |
| Maximum Mg chlorite per gram gel | 0 | 0.2 | 0.5 | 2.0 |

[1]LUQUASORB 1010, BASF Corp
[2]POLYOX WSR N3000, Dow Chemical Corp.

TABLE 3

| Component | Sample 5 | Sample 6 | Sample 7 | Sample 8 |
|---|---|---|---|---|
| Sodium carboxymethylcellulose (NaCMC)[1] | 0.75 | 0.75 | 0.73 | 0.73 |
| $Na_2HPO_4$ | 0 | 0 | 0 | 0.2 |
| Deionized water | 29.3 | 29.3 | 29.3 | 29.2 |
| S-Tab2 granules (−40 mesh) | 0 | 0.143 | 0.357 | 1.43 |
| Maximum Mg chlorite per g gel | 0 | 0.2 | 0.5 | 2.0 |

[1]Sigma Aldrich 419338

Each prepared sample was tested in accordance with USP <87>. The method involves determining the biological reactivity of mammalian cell cultures following contact with a topical gel product using an agar diffusion test. The cells in this test are L929 mammalian (mouse) fibroblast cells cultured in serum-supplemented MEM (minimum essential medium). A cell monolayer of greater than 80% confluence was grown at 37° C. in a humidified incubator for not less than 24 hours and then overlaid with agar. The agar layer serves as a "cushion" to protect the cells from mechanical damage, while allowing diffusion of leachable chemicals from the test specimen. Materials to be tested at applied to a piece of filter paper, which were then placed on the agar.

Specifically, a paper disk was dipped in sterile saline to saturate the disk. The amount of saline absorbed is determined (disk is weighed before and after wetting). A quantity of test specimen was dispensed onto the surface of the wetted disk. The specimen aliquot can be kept within the boundaries of the disk but is not spread out over the entire disk. The disk with the specimen aliquot was weighed again to assess the amount of sample on the disk. The disk was then placed on top of the agar overlay. Cultures are evaluated periodically over time for evidence of cytotoxicity and are graded on a scale of 0 (no signs of cytotoxicity) to 4 (severe cytotoxicity), as summarized in Table 4. A sample is deemed to meet the requirements of the test if none of the cell culture exposed to the sample shows greater than mild cytotoxicity (grade 2) after 48 hours of testing. A sample showing grade 3 or 4 reactivity during the 48 hours is deemed cytotoxic.

TABLE 4

| Grade | Reactivity | Description of Reactivity Zone |
|---|---|---|
| 0 | None | No detectable zone around or under specimen |
| 1 | Slight | Some malformed or degenerated cells under specimen |
| 2 | Mild | Zone limited to area under specimen |
| 3 | Moderate | Zone extends to 0.5 to 1.0 cm beyond specimen |
| 4 | Severe | Zone extends greater than 1.0 cm beyond specimen |

The volume tested of each prepared example in this experimental example was about 0.1 cc. The results are shown in Table 5.

TABLE 5

| Sample # | Gel Type | Maximum Mg chlorite per g gel | Test result |
|---|---|---|---|
| 1 | S | 0 | Pass |
| 2 |  | 0.2 | Pass |
| 3 |  | 0.5 | Fail |
| 4 |  | 2.0 | Fail |
| 5 | C | 0 | Pass |
| 6 |  | 0.2 | Pass |
| 7 |  | 0.5 | Fail |
| 8 |  | 2.0 | Fail |
|  | Positive control |  | Fail |
|  | Negative control |  | Pass |

Samples 1, 2, 5 and 6 met the criteria of USP biological reactivity in vitro, indicating biocompatibility. Samples 3, 4, 7 and 8 did not meet the requirements of the USP biological test in vitro. Thus, gels having a maximum concentration of chlorite anion greater than about 0.2 mg chlorite anion/gram gel produced cytotoxic effect in this experiment. These data suggest that cytotoxicity is related in a dose-dependent manner to the presence of chlorine dioxide, oxy-chlorine anions, or some other constituent(s) of S-TAB2 granules.

Experimental Example 2

Cytotoxicity Analysis

To confirm that cytotoxicity was induced by oxy-chlorine anions and not by other possibly noxious ingredients, the following experiment was performed.

A series of samples was prepared to test various ingredients or conditions for their role in inducing cytotoxicity. ASEPTROL S-Tab10 tablets were used to prepare some of the samples in this experiment. The chemical composition of the tablets is shown in Table 6. ASEPTROL S-Tab10 tablets were prepared essentially as described in Example 5 of U.S. Pat. No. 6,432,322.

TABLE 6

| Component | % (wt/wt) |
|---|---|
| Sodium chlorite | 26% |
| Dichloroisocyanuric acid, sodium salt | 7% |
| Sodium bisulfate | 26% |
| Sodium chloride | 20% |
| Magnesium chloride | 21% |

All of the samples comprised NaCMC as the thickener component. Samples 9, 16 and 17 were prepared using −40 mesh fraction granules prepared from ASEPTROL S-Tab10 tablets. Samples 10, 19 and 20 were prepared using the ingredients of ASEPTROL S-Tab 10 tablets in a non-granulated form. Specifically, the five ingredients were dried and mixed to form a powder having the composition shown in Table 5; the powder was not compacted and granulated. Thus, samples 9 and 10 have identical chemical composition but are made with the solid component in a different physical form. Similarly, samples 16 and 19 have identical compositions, as do samples 17 and 20, and samples 17 and 20, have the same chemical composition. Samples 11-14 were prepared using a powder having a subset of the ingredients in the ASEPTROL tablets, wherein one or more ingredients was replaced (see second column of Table 7 for details). Sample 15 contained substantially pure $ClO_2$. Sample 18 was NaCMC alone.

Samples 9-14 and 16-20 were prepared as described in Experimental Example 1. In brief, the samples were prepared by combining the solid fraction (e.g., ASEPTROL granules) with a base gel shortly before use. The base gel was NaCMC that was allowed to hydrate. After the solid fraction was added to the base gel, the samples were mixed for 30 seconds with a stainless steel or plastic spatula, capped, and left to stand at room temperature for 5 minutes. The samples were then mixed a second time for 30 seconds to homogenize the sample. Prepared samples were tightly capped until time of testing. The sodium chlorite granules and other solid mixture comprising sodium chlorite, and the prepared samples were protected from strong uv lights to limit uv-induced decomposition. Testing was begun no more than 2 hours after the samples were prepared.

Sample 15 was prepared using a base gel of hydrated NaCMC and a substantially pure chlorine dioxide solution that was prepared on the same day the sample was prepared and the test begun. The base gel was prepared by adding 0.75 gm of sodium carboxymethylcellulose powder (Sigma-Aldrich, 700,000 mole. wt., typ.) to 19.2 gm of deionized water, allowing the mixture to stand in a covered jar for overnight, and mixing to homogenize the base gel. The substantially pure chlorine dioxide solution was prepared as follows: Twelve (12) ASEPTROL S-Tab10 tablets (1.5 grams each) were placed into 1 liter of potable tap water, producing a deep yellow colored source solution of >1000 ppm chlorine dioxide. Air was bubbled into the bottom of the source solution at a rate of about 1 liter per minute to strip chlorine dioxide from the source solution into the air. The resultant chlorine dioxide-laden air was then bubbled into the bottom of 1 liter of deionized water to form a solution of pure chlorine dioxide. Only $ClO_2$ and possibly some water vapor was transferred from the source to the product solution. All the salt ingredients remained behind in the source solution. As a result, the product solution was a substantially pure solution of $ClO_2$. Bubbling was ended when the yellow color of the source solution was nearly gone. A sample of the substantially pure chlorine dioxide solution was analyzed for chlorine dioxide concentration using a Hach Model 2010 UV/Visible spectrophotometer; the substantially pure solution was found to contain 700 ppm chlorine dioxide by weight. Ten (10) grams of the 700 ppm pure chlorine dioxide solution was added to the base gel and mixed to produce a gel containing about 233 ppm chlorine dioxide and substantially no oxy-chlorine anions. As above, the $NaClO_2$-containing components and the prepared samples were protected from strong uv lights to limit uv-induced decomposition. All dry solid ingredients were protected from water exposure (e.g., ambient humidity) as well.

The samples were tested as described in Experimental Example 1, except samples 17 and 20 were tested at an 0.04 cc dose, rather than an 0.1 cc dose. Testing was begun no more than 2 hours after the samples were prepared.

The results are shown in Table 7.

TABLE 7

| Sample # | | Maximum Mg chlorite per gram final gel | Result of USP <87> |
|---|---|---|---|
| 9 | Prepared with ASEPTROL S-Tab10 granules | 0.5 | Fail |
| 10 | Prepared with non-granulated ingredients of ASEPTROL S-Tab10 | 0.5 | Fail |
| 11 | NaDCCA replaced with cyanuric acid | 0.5 | Fail |
| 12 | $NaClO_2$ replaced with NaCl | 0 | Pass |
| 13 | NaDCCA removed | 0.5 | Fail |
| 14 | $NaClO_2$ replaced with NaCl, and NaDCCA replaced with cyanuric acid | 0 | Pass |
| 15 | Prepared with pure $ClO_2$ (no other salts) | 0 | Pass |
| 16 | Sample 9 prepared with 3x the water | 0.17 | Fail |
| 17 | Sample 9, 0.04 cc dose on disk | 0.5 | Fail |
| 18 | NaCMC alone with no granules, salts or $ClO_2$ | 0 | Pass |
| 19 | Sample 10 prepared with 3x the water | 0.17 | Fail |
| 20 | Sample 10, 0.04 cc dose on disk | 0.5 | Fail |
| | Positive control | 0 | Fail |
| | Negative control | 0 | Pass |

Samples 9-11, 13, 16, 17, 19 and 20 all failed to meet the criteria for USP biological reactivity in vitro. Thus, mimicking the elution-type test of USP <87> did not alter the results (compare samples 10 and 19, and samples 9 and 16). Reducing the dose did alter the results (compare sample 9 and 17, and samples 10 and 20). These data indicate that neither the dose used in the test, nor the use of gel with 3x the water played a role in the observed cytotoxicity.

The results for samples 9 and 10 indicate that the physical form of the ASEPTROL component does not noticeably affect the cytotoxicity. The results for samples 11 and 13 indicate that the presence of a chlorine-producing agent, NaDCCA, does not noticeably affect the cytotoxicity. This result suggests that the observed cytotoxicity does not result from chlorine.

Samples 12, 14, 15, and 18 met the criteria for USP biological reactivity in vitro, indicating biocompatibility. These data indicate that the cytotoxicity is not caused by the gellent alone (Sample 18). The observation that Sample 15, which contained pure $ClO_2$ and no other salts, did not cause cytopathic effect indicates that chlorine dioxide itself is not the cause of cytotoxicity observed in the samples comprising ASEPTROL S-Tab10 granules.

The common feature of samples 12, 14, 15, and 18 is that none contains chlorite anion. Thus, none of samples 12, 14 and 18 contains oxy-chlorine anions. It is formally possible that sample 15, comprising pure $ClO_2$, may contain some oxy-chlorine anions due to the decomposition of $ClO_2$; however, the amount is insignificant.

In view of these results, it is concluded that oxy-chlorine anions are the causative agent underlying the cytotoxicity observed in these experiments.

Experimental Example 3

Cytotoxicity Analysis

The data in Experimental Example 1 indicate that the cytotoxicity of oxy-chlorine anions is dose dependent. Specifically, cytotoxicity was not observed in gels having a maximum of 0.2 mg chlorite anion per gram gel, whereas cytotoxicity was observed in gels having a maximum of 0.5 mg chlorite anion/gr. This experiment was designed to further examine the cytotoxicity of chlorite anions, using sodium chlorite solution, which permits an more accurate estimate of chlorite anion concentration in the thickened fluid compositions tested. In addition, the cytotoxicity of a commercially-available over-the-counter, peroxide-based, tooth whitening product, containing 10% hydrogen peroxide as the bleaching agent was also assessed.

Sample 22-24 were prepared by combining an aqueous solution of sodium chlorite with a base gel shortly before use. Thus, none of samples 22-25 contained chlorine dioxide. These samples also did not contain an acid source or a free halogen source. Samples 22-24 were prepared by mixing the aqueous sodium chlorite solution with the base gel for 30 seconds, capping the sample and letting it stand at room temperature for 5 minutes, the mixing for another 30 seconds. Sample 25 was similarly prepared but using water instead of a sodium chlorite solution. None of samples 22-25 contained an acid source or a free halogen source.

Sample 26 is an over-the-counter (OTC) product that is a gel containing 10% hydrogen peroxide; the gel material was used as present on the foil-wrapped strip.

Sample 21 was prepared using a substantially pure chlorine dioxide solution prepared by reacting ASEPTROL S-Tab10 tablets into water. Specifically, one 1.5 mg tablet was reacted in 200 mL $H_2O$. The resulting chlorine dioxide solution was not sparged. Chlorine dioxide concentration of the solution was about 733 ppm, as assessed using a Hach Model 2010 uv-vis spectrophotometer. Sample 21 thus had about 244 ppm $ClO_2$, after dilution of 1 part solution with 2 parts of gel The cytotoxicity results are shown in Table 8.

TABLE 8

| Sample # | Gel | Mg chlorite per gel | Result of USP <87> |
|---|---|---|---|
| 21 | CMC | 0 (Made with ~700 ppm $ClO_2$ solution) | Pass |
| 22 | | 0.04 | Pass |
| 23 | | 1.0 | Fail |
| 24 | | 2.0 | Fail |
| 25 | | 0 | Pass |
| 26 | unknown | OTC product with 10% hydrogen peroxide | Fail |
| Positive control | | | Fail |
| Negative control | | | Pass |

The results for Samples 22-24 indicate that chlorite anion at elevated concentration is cytotoxic to human cells, confirming the conclusions from Experimental Example 2. The result for Sample 21 indicates that a high chlorine dioxide concentration thickened fluid composition that is non-cytotoxic can be prepared using substantially pure chlorine dioxide solution prepared using ASEPTROL S-Tab10 tablets.

This data also shows that 10% $H_2O_2$ is cytotoxic (Sample 26) to mammalian cells. Indeed, the reactivity zone extended more than 1 cm beyond the gel specimen, suggesting severe cytotoxicity.

Experimental Example 4

Additional Cytotoxicity Studies

To further examine the relationship between cytotoxicity and oxy-chlorine anion concentration in a thickened fluid composition, the following experiment was performed.

Samples 27-31 were prepared by combining an aqueous solution of sodium chlorite (10 ml) with 20 g of a base gel (hydrated high viscosity NaCMC) shortly before use. The NaCMC was a USP grade CMC, obtained from Spectrum Chemical (stock # CA194); a 1% aqueous solution has a viscosity of about 1500-3000 cp. The base gel was prepared using 0.85 g. of NaCMC per 30 g final composition in order to achieve rheology equivalent to that for the CMC obtained from Sigma Aldrich. None of samples 27-30 contained chlorine dioxide. Sample 27 was similarly prepared but using water instead of a sodium chlorite solution. Samples 26-30 were prepared by mixing the aqueous sodium chlorite solution (or water) with the base gel until homogenous.

Sample 31, having the same relative composition as Sample 6 and about 40 ppm chlorine dioxide, was prepared using a two-syringe mixing method. One syringe contained –40 mesh ASEPTROL S-Tab2 granules (p. 048 g). The second syringe contained the base gel (10 grams). The contents of the two syringes were combined as follows. The syringe containing the granules was held with the tip pointing up. The outlet plug was removed and a nylon connector was attached. The other end of the nylon connector was attached to the outlet of the syringe containing the base gel. The plunger of the gel syringe was slowly depressed, expelling the gel into the granules. The gel-and-granules mixture was then allowed to sit for 5 minutes to activate the granules thereby generating chlorine dioxide; the syringes remained connected during this period. After 5 minutes, the syringe plungers were alternately depressed at a brisk rate to move the mixture back and forth between the two syringe bodies at least 15 times, or until the sample was homogenous in color. The gel was then ready for use the agar diffusion test of USP <87>.

The results of the cytotoxicity testing are shown in Table 9.

TABLE 9

| Sample # | Gel | Mg chlorite per gel | Result of USP <87> |
|---|---|---|---|
| 27 | CMC | 0 | Pass |
| 28 | | 0.1 | Pass |
| 29 | | 0.2 | Fail |
| 30 | | 0.4 | Fail |
| 31 | | 0.2* | Pass |
| Positive control | | | Fail |
| Negative control | | | Pass |

*Maximum amount of chlorite anion possibly present; calculated as described in Experimental Example 1

These data further support the discovery that chlorite anion is cytotoxic to human cells in a dose-dependent relationship. Sample 29, which contains 0.2 mg chlorite per gram final composition, failed the test, whereas Sample 28, which contains 0.1 mg chlorite anion per gram did not fail. This suggests that chlorine dioxide compositions having less than 0.2 mg chlorite anion per gram composition are not cytotoxic to human cells. This outcome also supports the expectation that chlorite anions present in gels made with ASEPTROL granules or powders is consumed in the generation of chlorine dioxide. Specifically, gels prepared using ASEPTROL granules or powder and having a maximum possible amount of 0.2 mg chlorite anion per gram final composition were found to be non-cytotoxic. Thus, the apparent concentration of chlorite anions in these gels is estimated to be less than 0.2 mg chlorite per gram.

Experimental Example 5

Tooth Whitening

Tooth whitening efficacy of a chlorine dioxide-containing CMC gel was assessed in the following experiment. The composition of the gel was substantially identical to that of Sample 6 in Table 3, having a maximum possible chlorite anion concentration of about 0.2 mg/gram final gel composition and about 40 ppm $ClO_2$. The results in Experimental Example 1 revealed that this composition is not substantially cytotoxic.

The materials and methods used in this experiment are now described.

Color assessment: Two methods were used to assess tooth shade: 1) visual assessment by Vita Classical Shade Guide; and 2) spectrophotometry. Digital imaging and digital image analysis was also performed to measure color of tooth images.

Visual assessment by Vita Classical Shade Guide: Initial baseline shade and subsequent shade change was assessed by direct comparison to a standard Vita shade guide. The Vita shade guide is arranged in the following order (as recommended by the manufacturer) for value assessment: B1*A1*B2*D2*A2*C1*C2*D4*A3*D3*B3*A3.5*B4*-C3*A4*C4, where B1 is the brightest and C4 is the darkest. Two investigators determined the closest shade match by visualizing the subject tooth against a standardized black background, under controlled, standardized fluorescent light conditions. In selected whitening experiments, background light conditions were standardized using a hand-held LED illuminating device at a fixed distance from the test specimen. The agreement level between operators in shade selection was greater than 80%. Disagreements in shade selection were never greater than 1 shade value unit (SVU).

Spectrophotometry: A clinical spectrophotometer, Vita Easy Shade® (Vident, Brea, Calif.) was used to obtain electronic, quantitative data about shade measurement and specific color measurement parameters based on the CIELAB L*a*b* color space. In this 3D color space system, "L" is the lightness of an object (ranging from black to white) and is the only dimension of color that may exist by itself; "a" is a measure of redness or green-ness; and "b" is a measure of yellowness or blueness. The device uses a D65 illuminant with a color temperature (in Kelvin) of 6500 degrees. At the conclusion of any whitening treatment, $\Delta L$, $\Delta a$, and $\Delta b$ values were determined and recorded.

Digital images: Digital images of the teeth were taken using an SLR digital camera/microscope (Olympus DPII Digital Camera/Microscope with Optiva Zoom 100 lens attachment). All images were obtained with standard manually-entered settings. Approximate fixed lighting of flash apparatus was configured to provide optimal, standardized imaging conditions. Samples were indexed or oriented repeatedly in a fixed orientation to insure reproducible image alignment.

Naturally-stained teeth: Human teeth having an intrinsic internal staining of D4 or lower (i.e., D4 through C4) were used as naturally-stained teeth. Teeth were sectioned then prepare as described below.

Tea-stained teeth: Human teeth with an intrinsic shade value greater than D4 (i.e., B1 through C2) were subjected to tea-based artificial staining solution as follows. After sectioning the teeth, the exposed dentin surfaces were polished with silicon carbide paper. The dentin surface was then etched with 37% phosphoric acid etching gel for 20-25 seconds, rinsed with water for 30 seconds, and blotted to a moist dentin condition. The teeth were then subjected to continuous staining cycles (by immersion in concentrated tea staining solutions) until the stain intensity appeared unchanged on visual inspection (usually in the Vita shade range of C4-A4).

Tea-stained and naturally-stained teeth were prepared for treatment as follows. The exposed dentin surfaces of the teeth were coated with three separate coats of clear nail polish; each coat was allowed to dry for at least one hour before the next coat was applied. Teeth were then placed in tap water for at least 24 hours prior to testing. Prior to initiation of treatment, baseline tooth segment shade was assessed by qualitative and quantitative color assessments. The teeth were mounted in mesio-distal orientation on a glass microscope slide. During treatments and between treatments, the teeth were stored in 100% humidity in a plastic bag. During the whitening assay, teeth were removed from the plastic bag, rinsed thoroughly to remove treatment or control whitening agent, then subjected to qualitative and quantitative color assessment.

Non-cytotoxic $ClO_2$ gel: The non-cytotoxic $ClO_2$ aqueous gel material tested was prepared substantially as described for Sample 6. In brief, thirty (30) grams of aqueous gel base was prepared by adding 0.85 grams of high viscosity sodium carboxymethylcellulose powder to 29.15 grams distilled water. The mixture was allowed to hydrate for at least about 8 hours, then was mixed to homogenize the base gel. To the about 30 grams aqueous NaCMC base gel in a container, 0.143 grams ASEPTROL S-Tab2 granules (~40 mesh) was added and mixed gently for 30 seconds. The container was then tightly capped and the mixture allowed to stand for 5 minutes at room temperature. It was then remixed briefly and the $ClO_2$ gel was then ready for use.

The concentrations of most of the constituents of the final gel can be calculated from mass balance or have been measured. The constituents are summarized in Table 10. The remaining constituents are: about 40 ppm $ClO_2$ by pH 7 titration and less than about 110 ppm un-reacted chlorite anion ($ClO_2$).

TABLE 10

| | Chemical species | | | | | | |
|---|---|---|---|---|---|---|---|
| | NaCMC | Water | $Na^+$ | $Mg^{+2}$ | Cl– | $SO_4^{-2}$ | Cyranuric acid |
| Conc., Weight % | 2.8% | 96.7% | 0.10% | 0.048% | 0.26% | 0.047% | 0.002% |

The prepared $ClO_2$ gel was a transparent to translucent, light yellow, viscous, pseudoplastic fluid. It had a yield point sufficient to retain its shape when applied in a 1-2 mm layer to teeth, but low enough to be substantially removed from the tooth surface and soft oral tissue by wiping. The gel was soluble in additional water and can be removed from the mouth via rinsing or irrigation. Although $ClO_2$ is unstable and will slowly decompose over time, the concentration loss over 8 hours under proper storage conditions (kept in closed container, tightly capped or sealed, and minimize exposure to ultraviolet radiation) is less than 20%.

Treatment: After mixing, the $ClO_2$ gel was drawn into a 60 ml plastic syringe. The 60 ml syringe was used to hold the gel during the assay, and for dispensing gel into a 10 ml plastic syringe. The gel in the 10 ml syringe was then dispensed directly onto the tooth section enamel surfaces as follows. At time zero, about 1 to 1.5 ml gel was dispensed onto the enamel surface of each tooth segment attached to the glass microscope slide. The thickness of the resulting gel layer was about 1.5 to 3.0 mm in depth. After dispensing the gel onto the tooth segments, the glass slide was placed in a 15 mm×8 mm plastic Ziplock® bag (SC Johnson Co., Racine, Wis.), containing small strips of wet paper towel within the bag to maintain 100% humidity in the bag. The paper towel strips were positioned to eliminate any contact of the plastic bag with the tooth and gel surfaces.

Upon conclusion of a testing interval (usually 15 minutes), the glass slide was removed from the plastic bag, and the gel was carefully removed with an extra soft bristle toothbrush and a gentle stream of running tap water. The tooth segments on the slide were then analyzed for shade and color, during which time the glass slide was maintained periodically in a plastic bag at 100% humidity to avoid undue color artifact resulting from dehydration.

The gel application procedure was repeated as designed until the experiment was concluded. The tested tooth segments were stored on the glass microscope slide in a 100% humidity for later reference observation.

Naturally-stained and tea-stained human teeth were treated with the $ClO_2$ gel for a total of one (1) hour (4-15 minute consecutive treatments). A single batch of $ClO_2$ gel was used for these consecutive treatments. For comparison, other tea-stained teeth were treated with an over-the-counter whitening product containing 10% hydrogen. Treatment with the OTC product consisted of 30 minute treatments, in accordance with the manufacturer's directions. At the end of a treatment, the residual OTC product left on the tooth after removal of the strip was removed from the tooth using a soft bristle toothbrush and a gentle stream of running water. For the multiple day treatments (e.g., 7, 10 and 14 days) using the OTC product, typically one 30 minute treatment occurred in the morning and the second 30 minute treatment occurred in the evening.

The Vita Shade values for individual teeth at baseline and after 4×15 minute treatments (total of 60 minutes) with $ClO_2$ gel are tabulated in Tables 11 and 12. One of the six tea-stained teeth and one of the six naturally-stained teeth each achieved B1 as a result of treatment with $ClO_2$ gel.

TABLE 11

Tea-stained teeth

| Specimen | Baseline shade | Post-treatment shade | SVUs |
|---|---|---|---|
| T1 | A4 | C1 | 9.0 |
| T2 | C2 | B1 | 6.0 |
| T3 | C4 | A3 | 7.0 |
| T4 | A3 | A2 | 9.0 |
| T5 | D3 | A2 | 5.0 |
| T6 | A4 | D2 | 11.0 |

TABLE 12

Naturally-stained teeth

| Specimen | Baseline shade | Post-treatment shade | SVUs |
|---|---|---|---|
| N1 | A3-D3 | D2-A2 | >4.0 |
| N2 | A3.5-B4 | B2 | >9.0 |
| N3 | A3 | B2-A1 | >6.0 |
| N4 | A3 | B2-A1 | >6.0 |
| N5 | A3 | B1 | 8.0 |
| N6 | B4 | A2 | 8.0 |

As shown in FIG. 1, after 30 minutes (2×15 minute treatments) of the non-cytotoxic $ClO_2$-containing gel on tea-stained teeth (n=6), the total shade change was well over 5 Shade Value Units-Vita (SVUs). For naturally-stained teeth (n=6), the total shade change was over 6 SVUs. After 45 minutes of treatment (3×15 minutes), the total shade change for naturally-stained teeth was about 7 SVUs. After one (1) hour (4×15 minute) of treatment of tea-stained teeth with the ASEPTROL gel, the mean total shade change was 7.83 SVUs. The total shade change for naturally-stained teeth treated with non-cytotoxic $ClO_2$ gel was about the same.

The non-cytotoxic $ClO_2$-containing gel achieved marked lightening of naturally-stained teeth after the first 15 minute treatment, and continued lightening with continued treatment. In contrast, treatment of naturally-stained teeth with the OTC composition containing 10% hydrogen peroxide showed a much lower degree of lightening. There was a modest improvement (1 SVU) observed after the first 30 minute treatment and no significant change after the second 30 minute treatment. Following the OTC product manufacturer's recommended 2×30 minute daily treatments for seven (7) days (total treatment time of 7 hours) resulted in a noticeable improvement (total shade change of 4.9 SVUs); however, the improvement in tooth whitening was markedly less compared to the $ClO_2$ composition after 4×15 minute consecutive treatments (total treatment time of 1 hour). Ten (10) days of treatment (2×30 min per day; total treatment time of 10 hours) with the OTC product yielded a total shade change of 6.1 SVUs. Fourteen (14) days of treatment (total treatment time of 14 hours) with the OTC composition containing 10% hydrogen peroxide was needed to result in a total shade change comparable to what was achieved with non-cytotoxic $ClO_2$ gel in one hour of treatment. Thus, the $ClO_2$-containing gel provided a greater degree of lightening in a significantly shorter time compared to the hydrogen peroxide-based composition. Furthermore, the $ClO_2$-containing gel formulation is non-cytotoxic, whereas the 10% hydrogen-peroxide formulation is cytotoxic (see Experimental Example 3).

The average $\Delta L$ value for tea-stained teeth treated for a total of one hour with $ClO_2$-containing gel was 9.3; the range of values for the 6 specimens was 0.8 to 22 $\Delta L$ units. The average $\Delta L$ value for naturally-stained teeth treated for a total of one hour with $ClO_2$-containing gel was 8.07. The average change in lightness for teeth treated for a total treatment time of 7 hours with the OTC composition containing 10% hydrogen peroxide was 6.32 $\Delta L$ units.

Thus, non-cytotoxic $ClO_2$-containing gel was extremely effective in bleaching tea-stained teeth and naturally-stained teeth. Notable improvement in lightening was detected after the first 15 minute treatment. The degree of lightening achieved after only two-15 minutes treatments with $ClO_2$-containing gel required 7 days of 2×30 minute daily treatments with an OTC whitening product containing 10% hydrogen peroxide to achieve. The degree of lightening achieved after four-15 minute treatments with $ClO_2$-containing gel required over 10 days of treatment with the OTC composition containing 10% hydrogen peroxide to achieve.

Experimental Example 6

Efficacy of $ClO_2$-Containing Gel Vs 36% Hydrogen Peroxide

This experiment was designed to compare the tooth whitening efficacy of a non-cytotoxic $ClO_2$-containing gel with a professional chair-side whitening gel containing 36% hydrogen peroxide. This is the highest concentration of hydrogen peroxide currently in use in professional chair-side products. The $ClO_2$-containing gel was prepared as described in Example 5 and the treatment procedure was the same as in Example 5.

Figure 2:
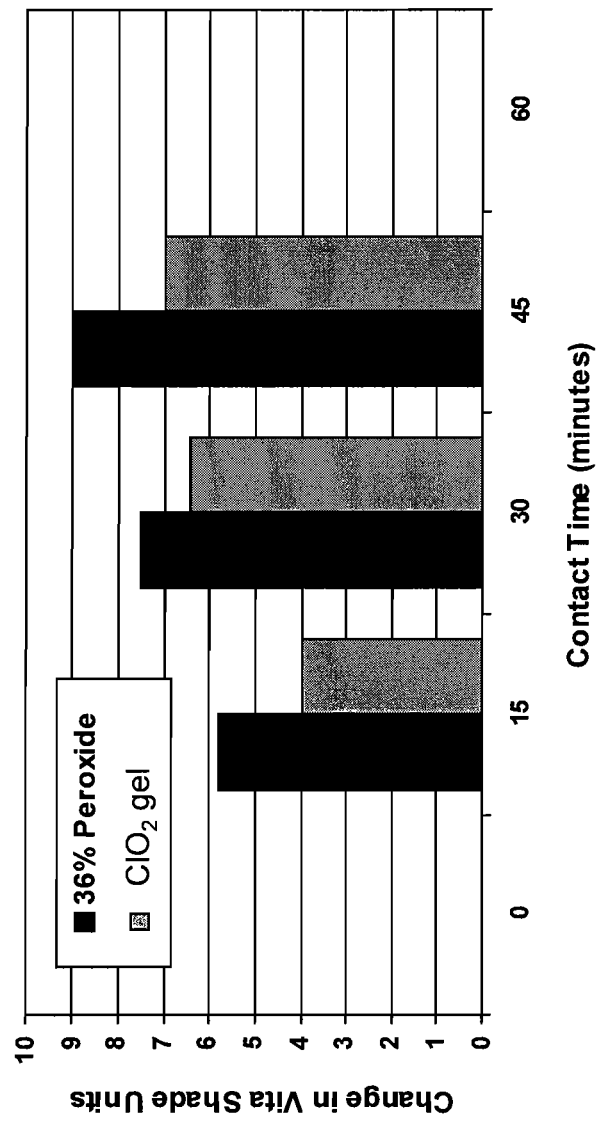
FIG. 2 is a graph depicting tooth whitening data for a non-cytotoxic $ClO_2$-containing composition in comparison to a professional whitening gel comprising 36% hydrogen peroxide as the bleaching agent.

The results are summarized in FIG. 2. After 45 minutes of treatment, the whitening efficacy of the non-cytotoxic $ClO_2$-containing gel (~40 ppm $ClO_2$) approached that of the professional gel. As is well known in the art, gels containing 36% hydrogen peroxide are highly irritating to soft tissue in the oral cavity. Thus, achieving comparable tooth whitening efficacy in the absence of soft tissue irritation is highly desirable and not possible with prior art products.

There are a variety of professional tooth whitening products on the market which are used by dental professionals. Like the over-the-counter products, the professional products are peroxide based. Data for the efficacy of these products is available in the literature (see for instance Operative Dentistry, 2007, 32-4: 322-327). The literature values suggest that a non-cytotoxic $ClO_2$-containing gel, a much milder bleaching agent than peroxide, approaches the efficacy of many peroxide-based professional products and, in some cases, may exceed the efficacy of peroxide-based professional products.

Experimental Example 7

Microhardness of Enamel and Dentin

Hydrogen peroxide is known to adversely affect tooth hard tissues. Tooth sensitivity is a common side effect of professional teeth whiten products and is believe to originate in morphological changes in the enamel and dentin induced by the high concentration of peroxide. Many professional products recommend the use of sodium fluoride to remineralize the teeth and potassium nitrate to reduce tooth sensitivity. To characterize the effect of a non-cytotoxic $ClO_2$-containing gel on enamel and dentin, the microhardness and roughness of enamel and dentin was assessed before and after contact with the chlorine dioxide-containing gel.

The composition of the $ClO_2$-containing gel is identical to the composition in Experimental 5. For both enamel and dentin experiments using the $ClO_2$-containing gel and an over-the-counter product (OTC) containing 10% $H_2O_2$, total treatment time was 7 hours, consisting of 14×30 minute treatments. Multiple batches of $ClO_2$-containing gel were prepared and used in this experiment. No batch of $ClO_2$-containing gel was used for more than 2 hours. The 7-hour total treatment time is the same as the treatment time recommended for the OTC product. However, this total treatment time is in great excess of the time needed to achieve tooth whitening with the non-cytotoxic chlorine dioxide composition comparable to OTC or professional peroxide-based products (see Examples 5 and 6). For the professional tooth whitening gel comprising 36% hydrogen peroxide, contact was limited to one hour. The tooth specimens were stored in tap water prior to, during and after treatment.

Microhardness was assessed using a CSM Dynamic Microhardness tester at 2 newtons load, 30 seconds load/30 second unloading. Five enamel specimens and five dentin specimens were tested for changes in microhardness. Each specimen served as its own control (pre-treatment compared to post-treatment). For enamel hardness, ten measurements per specimen were taken pre-treatment and post-treatment. Thus, there were 50 pre-treatment measurements and 50 post-treatment measurements. For dentin hardness, five measurements per specimen were taken pre-treatment and post-treatment, yielding 25 pre-treatment measurements and 25 post-treatment measurements. Microhardness data was calculated as Vickers hardness values. Statistical analysis consisted of ANOVA (one-way) using an alpha level of 0.05.

Results for enamel hardness (in Vickers hardness values) are shown in Table 13.

TABLE 13

| Composition | Pre-treatment | Post-treatment | p-value | Statistical significant ($p < 0.05$) |
|---|---|---|---|---|
| $ClO_2$-gel | 498.89 ± 70.64 | 507.40 ± 69.92 | 0.5090 | No |
| OTC product | 711.57 ± 114.56 | 722.84 ± 141.85 | 0.8474 | No |
| 36% $H_2O_2$ | 538.56 ± 109.30 | 455.72 ± 36.62 | 0.000768 | Yes |

Neither the $ClO_2$-containing gel nor the 10% $H_2O_2$ product induced a statistically significant change in enamel hardness. In contrast, the professional product induced a statistically-significant reduction (>15% reduction) in enamel hardness. Thus, non-cytotoxic $ClO_2$-containing gel whitens teeth with an efficacy comparable to that induced by professional peroxide gels but without adversely affecting enamel hardness.

Results for dentin microhardness (in Vickers hardness values) are shown in Table 14.

TABLE 14

| Composition | Pre-treatment | Post-treatment | p-value | Statistical significant ($p < 0.05$) |
|---|---|---|---|---|
| $ClO_2$-gel | 94.96 ± 9.63 | 87.65 ± 6.69 | 0.0031 | Yes |
| OTC product | 98.35 ± 15.14 | 88.71 ± 6.02 | 0.0118 | Yes |
| 36% $H_2O_2$ | 101.50 ± 21.48 | 83.45 ± 11.97 | 0.002212 | Yes |

Regarding dentin microhardness, the $ClO_2$-containing gel induced a minor (7.7%) reduction in dentin microhardness, which was statistically significant. The OTC product (10% peroxide) demonstrated a similar minor (9.8%) reduction in dentin microhardness, which was also statistically significant. Notably, the professional gel induced a dramatic (~18%) reduction in dentin after only one hour of total contact time.

Thus, non-cytotoxic composition comprising an efficacious amount of chlorine dioxide for tooth whitening has no statistically significant effect on enamel microhardness and only a minor effect on dentin microhardness. The effect on dentin microhardness is comparable to that induced by a commercially-available over-the-counter tooth whitening product.

Experimental Example 8

Surface Roughness of Enamel and Dentin

It has been suggested that increased roughness results in an increased surface area that facilitates rebound in whitened teeth. To study the effect of non-cytotoxic chlorine dioxide containing compositions on surface roughness, a Surftest 1700 Profilometer was used to assess surface roughness of enamel and dentin before and after treatment with various whitening compositions.

Four enamel specimens and four dentin specimens were tested. Each specimen served as its own control. Twelve measurements per specimen were taken pre-treatment and another twelve per specimen were taken post-treatment. Contact time for the $ClO_2$-containing gel was a total of 2.5 hours, consisting of 4-15 minute treatments and 3-30 minute treatments. Additional 30 minute treatments with $ClO_2$-containing gel were performed until a total treatment time of 7 hours was achieved. The specimens were stored in tap water prior to, during and after treatment. The non-cytotoxic chlorine dioxide-containing composition is the same as that used in Experimental Example 8. An over-the-counter (OTC) whitening product containing 10% hydrogen peroxide was also tested, in 14-30 minute consecutive treatments. A professional tooth whitening gel containing 36% hydrogen peroxide was also tested. For the professional tooth whitening gel, contact was limited to one hour. Statistical analysis consisted of ANOVA (one-way) using an alpha level of 0.05.

The profilometry data for the non-cytotoxic chlorine dioxide composition and the OTC product containing 10% hydrogen peroxide are shown in Table 15.

TABLE 15

|  |  | $R_a$ values | | | ANOVA | |
| --- | --- | --- | --- | --- | --- | --- |
|  |  | Pre- | Post-treatment | | p-value | |
|  |  | treatment | 2.5 hrs | 7 hrs | 2.5 hrs | 7 hrs |
| Enamel | OTC | 0.037692 ± 0.00914 | N/D | 0.048742 ± 0.0157 | N/D | 0.04674* |
|  | $ClO_2$ | 0.024975 ± 0.002445 | 0.021508 ± 0.000888 | 0.02295 ± 0.000666 | 0.005799* | 0.048636* |
| Dentin | OTC | 0.032053 ± 0.007332 | N/D | 0.051742 ± 0.00882 | N/D | 0.0000053* |
|  | $ClO_2$ | 0.03998 ± 0.005542 | 0.03775 ± 0.00466 | 0.044608 ± 0.00392 | 0.296884 | 0.027545* |

N/D = not determined.
*statistically significant

The average surface roughness, Ra, of enamel before treatment with the non-cytotoxic chlorine dioxide composition was about 0.025 and 0.021 after 2.5 hours of treatment, and about 0.023 after 7 hours of treatment. Thus, no adverse effect by the $ClO_2$-containing gel was detected on enamel average surface roughness, even despite extended duration of contact. Indeed, enamel average surface roughness was actually smoother by about 13-14% after 2.5 hours of $ClO_2$-containing gel treatment in this experiment, indicating an enamel polishing effect unexpected in the absence of an abrasive. Furthermore, the effect on dentin average surface roughness after 2.5 hours of treatment was statistically insignificant. After 7 hours of treatment, the increase in dentin average surface roughness was only about 8%. As previously noted, 7 hours of treatment is in excess of the time need to achieve tooth whitening with this composition comparable to OTC or professional peroxide-based products (see Examples 5 and 6). Thus, the non-cytotoxic chlorine dioxide composition can produce tooth whitening comparable to OTC or professional products without substantial damage to enamel or dentin surface roughness.

In contrast, OTC product-treated teeth after the recommended 7 hours of contact time showed an increase of enamel surface roughness of greater than about 29%. The increase in dentin surface roughness after 7 hours was greater than 60%. After only 1 hour of treatment, the professional peroxide product, containing 36% hydrogen peroxide, increased surface roughness of both enamel and dentin by about 203%.

Figures 3A, 3B, 3C:
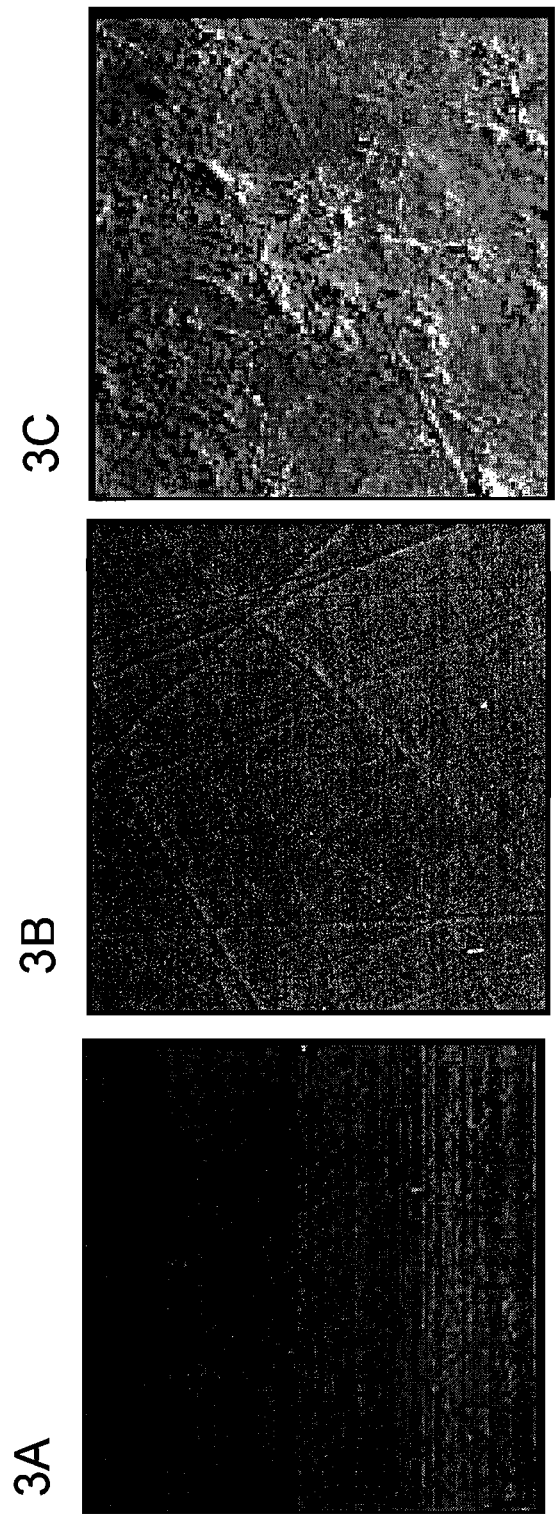
FIG. 3A-3C are a series of representative scanning electron microscopy (SEM) photomicrography images of enamel surface at 2500× magnification.

Regarding effect on enamel, there is little evidence of surface morphology alteration in enamel is observed in the specimen (FIG. 3B) treated with non-cytotoxic $ClO_2$-containing gel for 7 hours, compared to the non-treated control tooth (FIG. 3A). Indeed, the fine-finishing scratches (result of tooth specimen preparation) are still evident. In contrast, the photograph of the specimen (FIG. 3C) treated with the 36% peroxide gel for one hour reveals significant areas of enamel alteration and possible erosion.

Figures 4A, 4B, 4C:
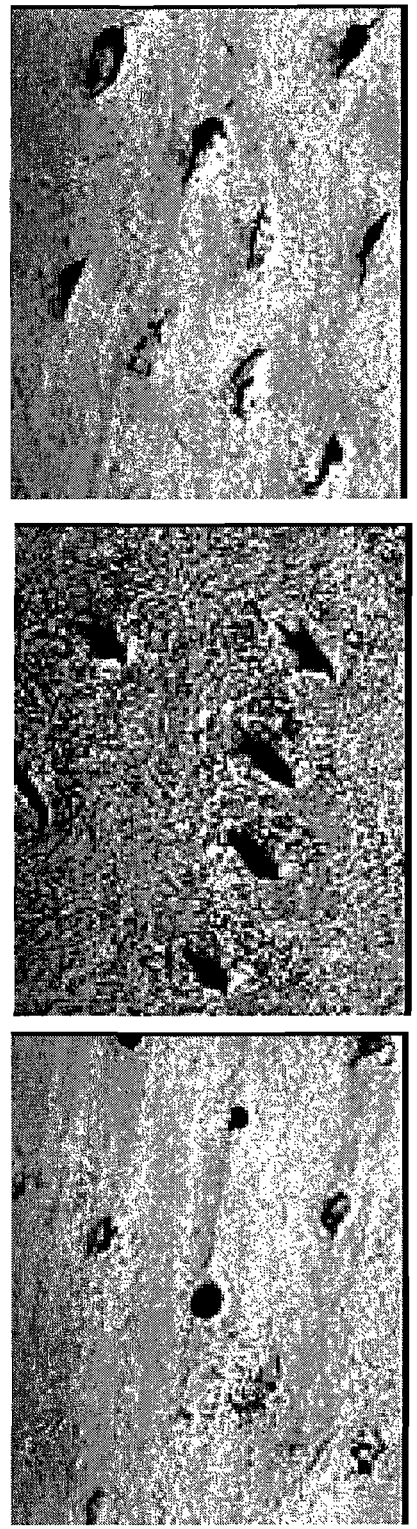
FIGS. 4A-4C are a series of representative SEM microphotograph images of dentin surface at 5000× magnification.

As shown in FIG. 4A, the dentin surface morphology of a control (untreated) tooth has some dentinal tubules exposed or revealed, with other dentinal tubules hidden by a dentin smear layer. Some smear plugs are evident within exposed tubules. The surface of the representative specimen treated with an OTC product containing 10% $H_2O_2$ (FIG. 4B) reveals a greater number of dentinal tubules exposed, compared with untreated control dentin surface. Exposed tubules appear somewhat enlarged compared to control surface, and many tubules appear open without the presence of occluding smear plugs. The representative tooth specimen (FIG. 4C) treated with non-cytotoxic $ClO_2$-containing gel has a greater number of dentinal tubules exposed or revealed, compared to control surface; but fewer in number and smaller in dimension than the tubules present in the OTC-treated specimen. Exposed tubules are present as narrow "slits" with limited openings; some dentinal tubules are hidden by an apparent smear layer; some smear plugs evident within exposed tubules. Thus, the surface of the tooth treated with non-cytotoxic $ClO_2$-containing gel more closely resembles the surface of the control tooth.

While not wishing to be bound by theory, it is believed that the alteration in dentin surface induced by the 10% hydrogen peroxide gel, and therefore expected for the higher concentration professional products, may underlie at least in part the tooth sensitivity issue common in over-the-counter and professional peroxide whitening products.

Experimental Example 9

Clinical Trial

The purpose of this human subject feasibility study is to evaluate the efficacy of a chair side, 1 hour (4 separate 15 minute treatments), in-office application of a non-cytotoxic tooth whitening composition comprising about 40 ppm chlorine dioxide and high viscosity sodium CMC as the thickener component. The composition will comprise no more than about 0.2 mg per gram composition oxy-chlorine anions. Shade change and tooth sensitivity to the tooth whitening agent, as well as patient response to the treatment, will be evaluated. Fifteen subjects will be enrolled in a clinical trial. Subjects will receive a 1 hour (4 separate 15-minute treatments), in-office treatment with the experimental tooth whitening agent in this pilot, single-arm, non-controlled, prospective, case-controlled study. All subjects will be monitored at baseline, immediately post-application of the in-office treatment, 72 hours post-application, and one week post application of the in-office treatment. Trained examiners using Vita (Vita Zahnfabrik) shade guides and color transparencies will monitor color changes. The Vita shade guide is one of the acceptable evaluation methods included in the ADA guidelines. The transparencies will be used as a record of color changes. Tooth sensitivity will be monitored using a standardized scale for the patient to mark at baseline, immediately post in office treatment, 72 hours post in office treatment and one week post in office treatment.

Subjects will be selected on the basis of having maxillary anterior teeth that are shade Vita A3 or darker, as judged by comparison with a value-oriented Vita shade guide. Subjects must be 18-65 years old, have good general health, and have good dental health and oral hygiene. Patients with active caries, periodontal disease, large anterior crowns or restorations, previously-bleached or tetracycline-stained teeth will be excluded from the study.

Upon acceptance into the study, each patient will be examined by one of the clinicians. A baseline Vita shade will be determined by two evaluators; the consensus shade of the six test maxillary anterior teeth and the six control mandibular teeth will be recorded by the dentist. A digital color transparency (Photomed S1 Pro Digital Clinical Camera—Fuji Body; Sigma Lens; Nikon Flash) will be made at a 1:1 magnification. The matching Vita shade tab will be included in the photograph.

An alginate impression of the maxillary arch will be made and poured in dental stone. Custom whitening trays will be fabricated for each patient using the material and design recommended by the manufacturer. All subjects will receive a prophylaxis before starting treatment and will be asked to mark a standardized scale to rate baseline sensitivity.

The clinical trial has been initiated, and preliminary data has been obtained.

The disclosures of each and every patent, patent application, and publication cited herein are hereby incorporated herein by reference in their entirety.

While the compositions, kits, and their methods of use have been disclosed with reference to specific embodiments, it is apparent that other embodiments and variations may be devised by others skilled in the art without departing from the true spirit and scope of the described compositions, kits and methods of use. The appended claims are intended to be construed to include all such embodiments and equivalent variations.

What is claimed is:

1. A composition for whitening a tooth surface, comprising chlorine dioxide, oxy-chlorine anions, a thickener component, an aqueous medium, and at least one of a sweetener and a flavorant, wherein the composition comprises at least about 20 ppm chlorine dioxide, no more than about 0.25 milligrams oxy-chlorine anion per gram composition and is substantially non-cytotoxic, and wherein the thickener component is selected from the group consisting of a natural hydrocolloid, a semisynthetic hydrocolloid, a clay, a high molecular weight polyethylene glycol, a high molecular weight polypropylene glycol, a polyethylene oxide, and a carbomer.

2. The composition of claim 1, wherein the thickener component is carboxymethylcellulose.

3. The composition of claim 1, wherein the composition comprises about 30 to about 1000 ppm chlorine dioxide.

4. The composition of claim 1, wherein the composition comprises less than about 0.2 milligrams oxy-chlorine anion per gram composition.

5. The composition of claim 1, wherein the composition has a pH from about 4.5 to about 11.

6. The composition of claim 1, wherein the thickener component is selected from the group consisting of a natural hydrocolloid, a semisynthetic hydrocolloid and a day.

7. The composition of claim 1, wherein the composition causes substantially no decrease in enamel or dentin microhardness of a tooth and/or substantially no increase in surface roughness of at least one of enamel and dentin.

* * * * *